US 6,734,420 B2

(12) United States Patent
Empedocles et al.

(10) Patent No.: US 6,734,420 B2
(45) Date of Patent: May 11, 2004

(54) DIFFERENTIABLE SPECTRAL BAR CODE METHODS AND SYSTEMS

(75) Inventors: Stephen A. Empedocles, Mountain View, CA (US); Joseph A. Treadway, Fremont, CA (US); Andrew R. Watson, Belmont, CA (US)

(73) Assignee: Quantum Dot Corporation, Hayward, CA (US)

( * ) Notice: Subject to any disclaimer, the term of this patent is extended or adjusted under 35 U.S.C. 154(b) by 235 days.

(21) Appl. No.: 09/827,013

(22) Filed: Apr. 5, 2001

(65) Prior Publication Data
US 2002/0022273 A1 Feb. 21, 2002

Related U.S. Application Data
(60) Provisional application No. 60/195,520, filed on Apr. 6, 2000.

(51) Int. Cl.[7] .............................................. G01N 21/29
(52) U.S. Cl. .................. 250/271; 250/458.1; 250/459.1
(58) Field of Search ............................. 250/271, 458.1, 250/459.1, 461.1

(56) References Cited

U.S. PATENT DOCUMENTS 6,108,463 A   8/2000  Herron et al.
6,492,125 B2  12/2002 Kauvar et al.

OTHER PUBLICATIONS

Http://www.chemsoc.org/cgi-shell/empower.exe, IUPAC Compendium of Chemical Terminology, *Chembytes Infozone*, (updated May 10, 1998) pp. 1–5.

Lakowicz, Joseph R., *Principles of Fluorescence Spectroscopy*—2nd Ed., ©1999 Kluwer Academic/Plenum Publishers, p. 3.

*Primary Examiner*—Albert Gagliardi
(74) *Attorney, Agent, or Firm*—Townsend & Townsend & Crew LLP; Mark D. Barrish, Esq.

(57) ABSTRACT

Devices, systems, methods, and compositions of matter can track and/or identify a library of elements, particularly for use with fluids, particulates, cells, and the like. Signals from one or more semiconductor nanocrystals may be combined to define spectral codes. Separation of signal wavelengths within dedicated wavelength ranges or windows facilitates differentiation of spectral codes, while calibration signals within the spectral codes can avoid ambiguity. Modeling based on prior testing can help derive libraries of acceptable codes.

78 Claims, 7 Drawing Sheets

DIFFERENTIABLE SPECTRAL BAR CODE METHODS AND SYSTEMS

CROSS-REFERENCES TO RELATED APPLICATIONS

The application claims the benefit of priority from co-pending U.S. Provisional Patent Application No. 60/195,520, entitled "Method for Encoding Materials with Semiconductor Nanocrystals, Compositions Made Thereby, and Devices for Detection and Decoding Thereof," filed Apr. 6, 2000, the full disclosure of which is incorporated herein by reference.

The subject matter of the present application is related to the following co-pending patent applications, the disclosures of which are also incorporated herein by reference: U.S. patent application Ser. No. 09/160,458 filed Sep. 24, 1998 and entitled, "Inventory Control"; U.S. patent application Ser. No. 09/397,432 filed Sep. 17, 1999, and also entitled "Inventory Control"; PCT Patent Application No. WO 99/50916 as published on Apr. 1, 1999, entitled "Quantum Dot White and Colored Light Emitting Diodes"; and U.S. patent application Ser. No. 09/259,982 filed Mar. 1, 1999, and entitled "Semiconductor Nanocrystal Probes for Biological Applications and Process for Making and Using Such Probes".

BACKGROUND OF THE INVENTION

The present invention generally provides devices, systems, methods, and kits for labeling and/or tracking inventories of elements. In a particular embodiment, the invention provides improved identification systems and methods which make use of labels that emit differentiable spectra, the spectra preferably including a number of signals having measurable wavelength maxima, minima, and/or intensities.

Tracking the locations and/or identities of a large number of items can be challenging in many settings. Barcode technology in general, and the Universal Product Code in particular, has provided huge benefits for tracking a variety of objects. Barcode technologies often use a linear array of elements printed either directly on an object or on labels which may be affixed to the object. These barcode elements often comprise bars and spaces, with the bars having varying widths to represent strings of binary ones, and the spaces between the bars having varying widths to represent strings of binary zeros.

Barcodes can be detected optically using devices such as scanning laser beams or handheld wands. Similar barcode schemes can be implemented in magnetic media. The scanning systems often electro-optically decode the label to determine multiple alphanumerical characters that are intended to be descriptive of (or otherwise identify) the article or its character. These barcodes are often presented in digital form as an input to a data processing system, for example, for use in point-of-sale processing, inventory control, and the like.

Barcode techniques such as the Universal Product Code have gained wide acceptance, and a variety of higher density alternatives have been proposed. Unfortunately, these known barcodes are often unsuitable for labeling many "libraries" or groupings of elements. For example, small items such as jewelry or minute electrical components may lack sufficient surface area for convenient attachment of the barcode. Similarly, emerging technologies such as combinatorial chemistry, genomics and proteomics research, microfluidics, micromachines, and other nanoscale technologies do not appear well-suited for supporting known, relatively large-scale barcode labels. In these and other ongoing work, it is often desirable to make use of large numbers of fluids, and identifying and tracking the movements of such fluids using existing barcodes is particularly problematic. While a few chemical encoding systems for chemicals and fluids had been proposed, reliable and accurate labeling of large numbers of small and/or fluid elements remained a challenge.

Small scale and fluid labeling capabilities have recently advanced radically with the suggested application of semiconductor nanocrystals (also known as Quantum Dot particles), as detailed in U.S. patent application Ser. No. 09/397,432, the full disclosure of which is incorporated herein by reference. Semiconductor nanocrystals are microscopic particles having size-dependent electromagnetic signal generation properties. As the band gap energy of such semiconductor nanocrystals vary with a size, coating and/or material of the crystal, populations of these crystals can be produced having a variety of spectral emission characteristics. Furthermore, the intensity of the emission of a particular wavelength can be varied, thereby enabling the use of binary or higher order encoding schemes. A label generated by combining semiconductor nanocrystals having differing emission signals can be identified from the characteristics of the spectrum emitted by the label when the semiconductor nanocrystals are energized.

While semiconductor nanocrystal-based inventory control schemes represent a significant advancement for tracking and identifying many elements of interest, still further improvements would be desirable. In general, it would be desirable to provide improved identification systems, methods for identifying elements, and/or identifiable groups or libraries of elements. It would be particularly beneficial if these improved inventory and identification systems enhanced the accuracy, reliability and robustness of the identifications provided by the system. Ideally, these improvements should allow enhanced differentiation of the labeled elements without significantly increasing the overall costs, complexity and/or size of the labels and associated system components. At least some of these objectives may be provided by the inventions described hereinbelow.

SUMMARY OF THE INVENTION

The present invention generally provides improved devices, systems, methods, kits, and compositions of matter for identification of elements of interest. The techniques of the present invention will often be adapted for use in tracking and/or identifying a large number or library of elements. These tracking or identification techniques are particularly well suited for use with fluids (such as liquids, solutions, gases, chemicals, biological fluids, and the like) and small items (such as jewelry, cells, components for assembly, and the like), but may also be used with a wide range of identifiable elements (including consumer products, powders, biological organisms, compositions of matter, and the like.) The inventory control techniques of the present invention will often make use of signals generated by one or more semiconductor nanocrystals. Semiconductor nanocrystals can be fabricated to absorb and/or emit signals at discrete wavelengths and intensities. The discrete signals from semiconductor nanocrystals can be combined to form a large number of differentiable spectral codes. More specifically, semiconductor nanocrystals can have absorption and emission characteristics that vary with their size and composition. By fabricating populations of semiconductor nanocrystals to generate signals at discrete wavelengths, the differing populations of semiconductor nanocrystals can be selectively combined to define labels having differentiable spectral codes.

While semiconductor nanocrystals are particularly advantageous for defining complex spectral codes, the labels may also comprise any of a wide variety of alternative signal-emitting or other markers, including organic or inorganic fluorescent dyes, Raman scattering materials, and the like. Regardless, the invention enhances the robustness of the spectral codes by a variety of techniques, including the addition of calibrating signals within the label spectra as an aid for code interpretation. This calibration signal can compensate for overall signal variability in wavelength and/or in intensity. Surprisingly, the invention also enhances the number of differentiable codes by limiting the label spectra to a series of signals having discrete wavelengths within separated wavelength ranges or windows, thereby facilitating identification of substantially isolated peak wavelengths from among tightly spaced discrete allowable wavelength increments. The invention also provides methods for establishing an inventory of acceptable labels by either physically testing candidate spectral labels, or by modeling the characteristics of the spectral labels and/or label interpreting system to help insure that the system can accurately differentiate between the different elements of the inventory based on the spectra of the labels.

In a first aspect, the invention provides an identification system. The identification system comprises a plurality of identifiable elements and a plurality of labels. Each label is associated with an identifiable element, and the labels include reference markers and other markers, the labels generating spectra in response to excitation energy. An analyzer identifies the elements from the spectra of the associated labels by calibrating the spectra using reference signals generated by the reference markers.

In many embodiments, the labels comprise semiconductor nanocrystals, with the reference markers often including at least one reference semiconductor nanocrystal. The reference markers may include a plurality of reference semiconductor nanocrystals, the reference markers of each label generating a reference wavelength with a reference intensity. Similarly, the other markers may comprise other semiconductor nanocrystals generating associated signals at associated wavelengths and with associated intensities. The spectra may define an identifiable spectral code, with the other markers optionally comprising code signal markers, the spectra comprising a combination of the reference signals from the reference markers in combination with code signals from the code signal markers Optionally, the analyzer can, for each label, discretely quantify the other signals of the label by comparison of the other signals with the reference signal. For example, where the reference signal has a reference intensity and the other signals of the label have other intensities, the analyzer can discretely quantify the other intensities by comparison to the reference intensity of that label. This is particularly beneficial when interpreting spectral codes which employ variations in both wavelength and intensity. The intensities may define discrete intensity ratios relative to the associated reference intensities. For example, the other intensities may be integer multiples of the reference intensity, or a variety of regular intensity ratio increments may be provided, with each signal from the other markers having an intensity selected from ½, 1, 1.5, . . . or 3.5 times the intensity of the reference signal. In some embodiments, the signals from the other markers may have an arbitrary, and typically known, intensity relative to the intensity of the reference signal.

To facilitate identification of the reference signal, the reference intensity may be a highest or lowest intensity of the label spectra. Alternatively, at least some of the labels may have a common reference signal wavelength. A variety of alternative reference signal identification criteria may be established, such as selecting a shortest or longest wavelength of the spectra of the label as the reference wavelength, and the like. The analyzer may be adapted to identify the reference signal based on a pre-determined criteria.

Advantageously, the spectral identification system of the present invention is particularly well-suited for use with large numbers of identifiable elements. Typically, the identification system will include at least 10 elements, often having at least 100 elements, often having at least 1,000 elements, and in many embodiments, having at least 10,000 identifiable elements. As the invention enhances the robust interpretation of complex spectral codes, large numbers of such codes may be reliably interpreted with the aid of a calibration signal within the spectra. Nonetheless, the invention may find uses with identification systems having fewer numbers of labels.

In many embodiments, the analyzer will comprise a tangible media embodying a machine-readable code comprising a listing of a plurality of distinguishable labels. Often times, the code will also include a listing of the identifiable elements, and can provide a correlation between each label and an associated identifiable element having the label. The identifiable elements may comprise compositions of matter, fluids, articles of manufacture, consumer products, components for an assembly, and a wide variety of alternative items of interest.

In a related method aspect, the invention provides a method for sensing a plurality of identifiable elements. The method comprises labeling each identifiable element with a reference marker and at least one associated other marker. The markers of a first label from a first identifiable element are energized so that the markers generate signals. A spectrum defined by the combined signals is measured from the first identifiable element. The first identifiable element is identified from the measured spectrum by calibrating the spectrum with reference to a reference signal from the reference marker of the first label.

In another related aspect, the invention provides a library of elements. The library comprises a plurality of identifiable elements, each identifiable element having an associated label with a reference marker. The labels generate spectra in response to an excitation energy. Each spectrum includes a wavelength calibration reference signal from the reference marker.

In another aspect, the invention provides a method comprising labeling an identifiable element with a label, and measuring a spectrum generated by the label. The spectrum comprises a plurality of signals. The element is identified by selecting a first wavelength range encompassing a first signal of the spectra, and by determining a wavelength of the first signal within the first range. Typically, the wavelength of the signal will comprise wavelength having a local and/or overall maximum intensity, often referred to as the peak wavelength of the signal.

Often times, the element will be labeled by applying at least one semiconductor nanocrystal to the element. The semiconductor nanocrystals generate at least some of the signals of the spectra in response to excitation energy.

The method will often further comprise selecting a second wavelength range encompassing a second signal of the spectra, and determining a wavelength of the second signal within the second range. Still further additional wavelength ranges may be selected, and wavelengths identified for each additional signal of the spectra within its associated range. Preferably, no more than one signal of the spectra will be disposed within each wavelength range. By limiting the number of signals within a wavelength range, the various signals of the spectra can be sufficiently separated to avoid excessive overlap of adjacent signals. This allows wavelengths of the signals within each associated wavelength range to be readily identified, even when the signals can occupy any of a plurality of relatively tightly spaced discrete wavelength increments. Accurate selection of an appropriate predetermined wavelength for each signal is significantly facilitated by limiting spacing between adjacent signals.

Typically, the wavelengths of the first and second signals will be determined by selecting the wavelengths of the signals from a plurality of discrete wavelengths within the ranges. The discrete wavelengths within each range can be sufficiently close that if two signals were at adjacent discrete wavelengths within the range they would substantially overlap, optionally overlapping sufficiently to make identification of either or both wavelength peaks of the signals difficult and/or impossible.

In many embodiments, the discrete wavelengths within the ranges will be predetermined. These discrete wavelengths may be separated by about 1 nanometer or more, generally being separated by about 5 nanometers or more, optionally being separated by about 15 nanometers or more, and in many embodiments, being separated by about 30 nanometers or more.

Typically, the wavelength ranges will be separated, ideally being sufficiently separated so that a pair of signals at adjacent discrete wavelengths within two different ranges can have their discrete wavelengths identified independently and relatively easily. Typically, the ranges will be separated by at least about 30 nm, often by at least about 50 nm, and each wavelength range will include at least 1, and often at least 5 predetermined discrete wavelengths. To accommodate relatively large numbers of spectral codes, there will often be at least three non-overlapping ranges, with the wavelength ranges optionally being predetermined. In other embodiments, the wavelength ranges may not be separated. In such embodiments, the encoding system may optionally have signals within two adjacent wavelength ranges separated by at least a predetermined wavelength separation, wavelengths within adjacent ranges typically being separated by at least 30 nm, often being separated by at least about 50 nm.

Optionally, the wavelength may be determined by deciding whether a discrete wavelength is present or absent. Such binary methods will often make use of labels having at least one different signal for each different label. Alternatively, a discrete intensity of at least one wavelength may be measured to provide a higher-order code with more information for a given spectral range.

Where differing materials and their associated labels are to be intermingled, the signals of a first label may optionally be encompassed within a first wavelength range, while the signals of a second label are encompassed within another wavelength range. Separation of the first and second wavelength ranges can help avoid confusion between the intermingled markers of the two labels, allowing each identifiable element to be independently identified.

In a related method aspect, the invention provides a method for sensing a plurality of intermingled labels. The method comprises energizing the labels so that the labels generate signals. A first label is identified by measuring a first discrete wavelength from among a plurality of discrete wavelengths within a first wavelength range. A second label is identified by measuring a second discrete wavelength from among a plurality of discrete wavelengths within a second wavelength range, the first and second wavelength ranges being separated.

Separation of differing wavelengths of differing labels into separate wavelength ranges or windows is particularly useful when tracking fluids which are to be combined. For example, when any of a first plurality of fluids is to be added to any of a second plurality of fluids, maintaining the spectral codes of each group of fluids within a dedicated window can significantly facilitate identification of each fluid in the combination. Similarly, labels may be attached at each process step of a multi-step method so as to indicate the specific processes performed.

In yet another aspect, the invention provides an inventory system comprising a plurality of identifiable elements. A plurality of labels have markers, with each label associated with an element. Each marker generates a signal when energized so that each label emits an identifiable spectrum. At least some of the spectra comprise a plurality of signals, with each signal of the spectra having a discrete wavelength selected within a dedicated wavelength range. The ranges are sufficiently separated so that the signals in different ranges are independently identifiable.

In yet another aspect, the invention provides an inventory label method. The method comprises generating a plurality of candidate labels, and selecting a plurality of acceptably distinguishable labels from among the candidate labels. The acceptable labels are selected by determining spectra emitted by the candidate labels when the candidate labels are energized, and by comparing the spectra of the candidate labels.

Candidate labels may be generated by physically combining a plurality of markers, where each marker emits a marker signal at an associated signal wavelength in response to excitation energy. This also allows the spectra of the labels to be measured by directing excitation energy towards the markers. Alternatively, the spectra of the candidate labels may be determined by modeling a combination of a plurality of marker signals. The individual marker signals may be separately measured, or the marker signals may be calculated by modeling emissions from a manufacturable marker. Preferably, the calculated signals may be adjusted for spectra analyzer characteristics and/or variations of measured marker signals. Often times, at least some of the candidate codes will be compared with a library of distinguishable codes to determine if the candidate codes are acceptable, and the acceptable candidate codes can be added to the library.

In yet another aspect, the invention provides a method for identifying a plurality of identifiable elements. The method comprises energizing a plurality of labels so that a first marker of each label generates a first signal with a first wavelength peak. At least some of the labels comprise multiple-signal labels, and each multiple-signal label has a second marker generating a second signal with a second wavelength peak. The first wavelength peaks are measured, and the second wavelength peak of each multiple-signal label can be measured at a predetermined minimum wavelength separation (or more) from the associated first peak. The labels can then be identified in response to the measured peaks. Generally, each predetermined minimum wavelength separation is at least as large as a full width half maximum (FWHM) of one ore both of the peaks separated thereby.

DESCRIPTION OF THE SPECIFIC EMBODIMENTS

The present invention generally provides improved devices, systems, methods, compositions of matter, kits, and the like for identifying and/or tracking one or more particular items or elements of interest. The invention can take advantage of recently enhanced capabilities of new compositions of matter at generating signals in response to excitation energy. A particularly advantageous signal generation structure for use with the present invention is the semiconductor nanocrystal. Other useful signal emitting structures may also take advantage of the improvements provided by the present invention, including conventional fluorescent dyes, radioactive and radiated elements and compounds, Raman scattering materials (with or without surface enhancement and/or resonant signal excitation) and the like. The invention can be used to calibrate spectral codes formed of multiple signals, significantly facilitating interpretation and accurate reading of the emitted spectra. The invention may also enhance the clarity of codes by the use of improved encoding techniques which involve separating discrete signal peaks within a spectrum. The enhanced robustness of such a separated code may be used to pack more information into a spectral code, enhance the accuracy and reliability of the code, and/or allow simplification of the coding process (for example, by allowing sufficient information to be transmitted spectrally using a binary code in which a signal is either present or absent at a particular wavelength, rather than relying on proper intensity level interpretation). The invention can also facilitate the generation of spectral codes as well as the generation of an inventory of labels suitable for spectral identification.

Spectral Labeling of Libraries

Figure 1:
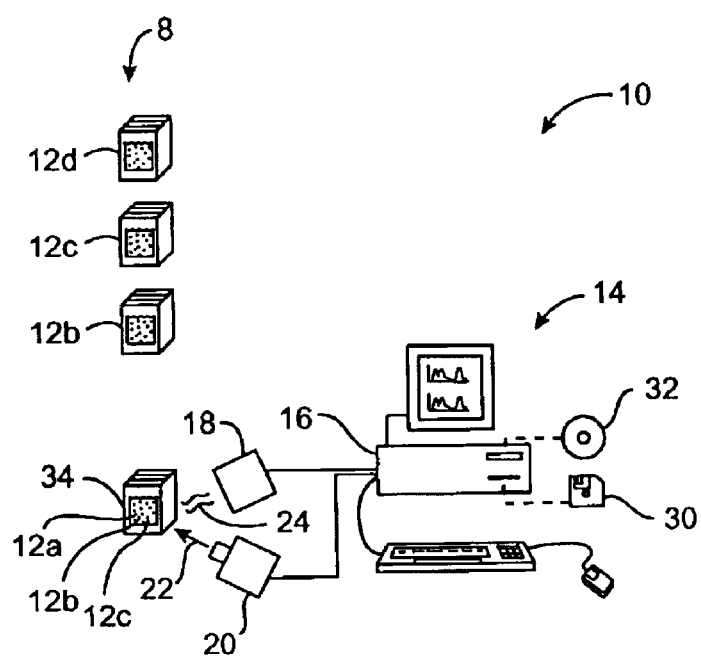
FIG. 1 schematically illustrates an inventory system and identification method according the principles of the present invention.

Referring now to FIG. 1, an inventory system 10 includes a library 8 of labeled elements 12 and an analyzer 14. Analyzer 14 generally includes a processor 16 coupled to a sensor 18. An energy source 20 transmits an excitation energy 22 to a first labeled element 12a. In response to excitation energy 22, first labeled element 12a emits radiant energy 24 defining a spectral code. The spectral code of radiant energy 24 is sensed by sensor 18, and the spectral code is interpreted by processor 16 so as to identify labeled element 12a.

Library 8 may optionally comprise a wide variety of items of interest. In many embodiments, labeled elements 12a, 12b, 12c, 12d, ... (collectively referred to as elements 12) may be separated. Analyzer 14 may be used to individually and/or sequentially identify such separated elements 12. In other embodiments, the various labeled elements 12a, 12b, 12c ... are sensed simultaneously, such as when the labeled elements are intermingled within a test fluid 34. A plurality of the elements 12 of library 8 may be identified simultaneously by, for example, simultaneously imaging spectra generated by the plurality of elements with sensor 18. In many embodiments, maintaining each label as a spatially separated unit will facilitate identification of the spectra, this spatial separation being encompassed within the term "spatially resolved." Preferably, the spatial integrity of the elements and the space between elements will be sufficient to allow at least some of the elements to be individually resolved over all other elements, preferably allowing most of the elements to be individually resolved, and in many embodiments, allowing substantially all of the elements to be individually resolved. As imaging is facilitated by maintaining the labeled elements on or near a surface, fluid 34 may be contained in a thin, flat region between planar surfaces.

The spectral coding of the present invention is particularly well-suited for identification of small or fluid elements which may be difficult to label using known techniques. Elements 12 may generally comprise a composition of matter, molecules, a fluid, an article of manufacture, a consumer product, a component for an assembly, a bead, a cell or biological organism, or the like.

The labels included with labeled elements 12 may be adhered to, applied to a surface of, and/or incorporated within the elements or items of interest, optionally using techniques analogous to those of standard bar coding technologies. For example, spectral labeling compositions of matter (which emit the desired spectra) may be deposited on adhesive labels and applied to articles of manufacture. Alternatively, an adhesive polymer material incorporating the label might be applied to a surface of a small article, such as a jewel or a component of an electronic assembly. As the information in the spectral code does not depend upon the aerial surface of the label, such labels can be quite small.

In other embodiments, the library will comprise fluids such as biological samples, powders, cells, and the like. While labeling of such samples using standard bar coding techniques can be quite problematic, particularly when a large number of samples are to be accurately identified, the spectral bar codes of the present invention can allow robust identification of a particular element from among ten or more library elements, a hundred or more library elements, a thousand or more library elements, and even ten thousand or more library elements.

The labels of the labeled elements 12 will often include compositions of matter which emit energy with a controllable wavelength/intensity spectrum. To facilitate identification of specific elements from among library 8, the labels of the elements may include combinations of differing compositions of matter to emit differing portions of the overall spectral code. In other embodiments, the signals may be defined by absorption (rather than emission) of energy, by Raman scattering, or the like. As used herein, the term "markers" encompasses compositions of matter which produce the different signals making up the overall spectra. A plurality of markers can be combined to form a label, with the signals from the markers together defining the spectra for the label. The present invention generally utilizes a spectral code comprising one or more signals from one or more markers. The markers may comprise semiconductor nanocrystals, with the different markers often taking the form of particle size distributions of semiconductor nanocrystals having different characteristic spectral emissions or marker signals. The combined markers define labels which can emit spectral codes, which are sometimes referred to as "spectral barcodes." These barcodes can be used to track the location of a particular item of interest or to identify a particular item of interest.

The semiconductor nanocrystals can be tuned to a desired wavelength to produce a characteristic spectral emission or signal by changing the composition and/or size of the semiconductor nanocrystal. Additionally, the intensity of the emission at a particular characteristic wavelength can also be varied (optionally by, at least in part, varying a number of semiconductor nanocrystals emitting at a particular wavelength), thus enabling the use of binary or higher order encoding schemes. The information encoded by the semiconductor nanocrystals can be spectroscopically decoded, thus providing the location and/or identity of the particular item or component of interest. As used herein, wavelength and intensity are encompassed within the term "signal characteristics." A first range is "separated" from a second range when the first range is both non-overlapping and discontinuous from the second range so that there is an intermediate range between the first range and the second range.

While spectral codes will often be described herein with reference to the signal characteristics of signals emitted with discrete, narrow peaks, it should be understood that semiconductor nanocrystals and other marker structures may generate signals having quite different properties. For example, signals may be generated by scattering, absorption, or the like, and alternative signal characteristics such as wavelength range, width, slope, shift, or the like may be used in some spectral coding schemes.

Semiconductor Nanocrystals

Semiconductor nanocrystals are particularly well-suited for use as markers in a spectral code system because of their unique characteristics. Semiconductor nanocrystals have radii that are smaller than the bulk exciton Bohr radius and constitute a class of materials intermediate between molecular and bulk forms of matter. Quantum confinement of both the electron and hole in all three dimensions leads to an increase in the effective band gap of the material with decreasing crystallite size. Consequently, both the optical absorption and emission of semiconductor nanocrystals shift to the blue (higher energies) with decreasing size. Upon exposure to a primary light source, each semiconductor nanocrystal distribution is capable of emitting energy in narrow spectral linewidths, as narrow as 15–30 nm, and with a symmetric, nearly Gaussian line shape, thus providing an easy way to identify a particular semiconductor nanocrystal. The linewidths are dependent on the size heterogeneity, i.e., polydispersity, of the semiconductor nanocrystals in each preparation. Single semiconductor nanocrystal complexes have been observed to have full width at half maximum peak intensities (FWHM) as narrow as 12–15 nm. In addition semiconductor nanocrystal distributions with larger linewidths in the range of 40–60 nm can be readily made and have the same physical characteristics as semiconductor nanocrystals with narrower linewidths.

Exemplary materials for use as semiconductor nanocrystals in the present invention include, but are not limited to group I–VII, II–VI, III–V, and group IV semiconductors such as ZnS, ZnSe, ZnTe, CdS, CdSe, CdTe, GaN, GaP, GaAs, GaSb, InP, InAs, InSb, AlS, AlP, AlSb, PbS, PbSe, Ge, Si, and ternary and quaternary mixtures or alloys thereof, as well as compositions involving these materials doped with other elements such as transition metals (e.g., yttrium vanadate doped with lanthanides). The semiconductor nanocrystals are characterized by their nanometer size. By "nanometer" size, it is meant less than about 150 Angstroms (Å), and preferably in the range of 12–150 Å.

The selection of the composition of the semiconductor nanocrystal, as well as the size of the semiconductor nanocrystal, affects the signal characteristics of the semiconductor nanocrystal. Thus, a particular composition of a semiconductor nanocrystal as listed above will be selected based upon the spectral region being monitored. For example, semiconductor nanocrystals that emit energy in the visible range include, but are not limited to, CdS, CdSe, CdTe, and ZnTe. Semiconductor nanocrystals that emit energy in the near-IR range include, but are not limited to, CdTe, InP, InAs, InSb, PbS, and PbSe. Finally, semiconductor nanocrystals that emit energy in the blue to near-ultraviolet include, but are not limited to, ZnS and GaN. For any particular composition selected for the semiconductor nanocrystals to be used in the inventive system, it is possible to tune the emission to a desired wavelength within a particular spectral range by controlling the size of the particular composition of the semiconductor nanocrystal.

In addition to the ability to tune the signal characteristics by controlling the size of a particular semiconductor nanocrystal, the intensities of that particular emission observed at a specific wavelength are also capable of being varied, thus increasing the potential information density provided by the semiconductor nanocrystal coding system. In some embodiments, 2–15 different intensities may be achieved for a particular emission at a desired wavelength, however, more than fifteen different intensities may be achieved, depending upon the particular application of the inventive identification units. For the purposes of the present invention, different intensities may be achieved by varying the concentrations of the particular size semiconductor nanocrystal attached to, embedded within or associated with an item or component of interest, by varying a yield of the nanocrystals, by varyingly quenching the signals from the semiconductor nanocrystals, or the like. Nonetheless, the spectral coding schemes may actually benefit from a simple binary structure, in which a given wavelength is either present our absent, as described below.

In a particularly preferred embodiment, the surface of the semiconductor nanocrystal is also modified to enhance the efficiency of the emissions, by adding an overcoating layer to the semiconductor nanocrystal. The overcoating layer is particularly preferred because at the surface of the semiconductor nanocrystal, surface defects can result in traps for electron or holes that degrade the electrical and optical properties of the semiconductor nanocrystal. The overcoating layer provides electronic and chemical insulation for the emissive core and removes or energetically displaces surface trap sites. This results in higher efficiency in the luminescent process and/or greater chemical/photochemical stability.

Suitable materials for the overcoating layer include semiconductors having a higher band gap energy than the semiconductor nanocrystal. In addition to having a band gap energy greater than the semiconductor nanocrystals, suitable materials for the overcoating layer should have good conduction and valence band offset with respect to the semiconductor nanocrystal. Thus, the conduction band is desirably higher in energy and the valence band is desirably lower in energy than those of the semiconductor nanocrystal. For semiconductor nanocrystals that emit visible light (e.g., CdS, CdSe, CdTe, ZnSe, ZnTe, GaP, GaAs) or near-IR (e.g., CdTe, InP, InAs, InSb, PbS, PbSe), a material that has a band gap energy in the ultraviolet regions may be used. Exemplary materials include ZnS, GaN, and magnesium chalcogenides, (e.g., MgS, MgSe, and MgTe). For semiconductor nanocrystals that emit in the near IR, materials having a band gap energy in the visible, such as CdS, or CdSe, may also be used. While the overcoating will often have a higher bandgap than the emission energy, the energies can be, for example, both within the visible range. The overcoating layer may include from 0.1 to 10 monolayers of the overcoating material. The preparation of a coated semiconductor nanocrystal may be found in U.S. patent application Ser. No. 08/969,302 filed Nov. 13, 1997, entitled "Highly Luminescent Color-Selective Materials"; Dabbousi et al., *J. Phys. Chem B.,* Vol. 101, 1997, pp. 9463; Kuno et al., *J. Phys. Chem.,* Vol. 106, 1997, pp. 9869; and International Publication No. WO 99/26299, published on May 27, 1999. Fabrication and combination of the differing populations of semiconductor nanocrystals may be further understood with reference to U.S. patent application Ser. No. 09/397,432, previously incorporated herein by reference.

It is often advantageous to combine different markers of a label into one or more labeled body. Such labeled bodies may help spatially resolve different labels from intermingled items of interest, which can be beneficial during identification. These label bodies may comprise a composition of matter including a polymeric matrix and a plurality of semiconductor nanocrystals, which can be used to encode discrete and different absorption and emission spectra. These spectra can be read using a light source to cause the label bodies to absorb and/or emit light. By detecting the light absorbed and/or emitted, a unique spectral code may be identified for the labels. In some embodiments, the labeled bodies may further include markers beyond the label bodies. These labeled bodies will often be referred to as "beads" herein, and beads which have assay capabilities may be called "probes." The structure and use of such probes, including their assay capabilities, are more fully described in U.S. patent application Ser. No. 09/566,014, previously incorporated by reference.

Fabrication of Labeled Beads

A process for encoding spectra into label body materials using a feedback system can be based on the absorbance and luminescence of the semiconductor nanocrystals in a solution that can be used to dye the materials. More specifically, this solution can be used for encoding of a plurality of semiconductor nanocrystals into a material when that material is a polymeric bead.

A variety of different materials can be used to prepare these compositions. In particular, polymeric bead materials are an appropriate format for efficient multiplexing and demultiplexing of finite-sized materials. These label body beads can be prepared from a variety of different polymers, including but not limited to polystyrene, cross-linked polystyrene, polyacrylic, polysiloxanes, polymeric silica, latexes, dextran polymers, epoxies, and the like. The materials have a variety of different properties with regard to swelling and porosity, which are well understood in the art. Preferably, the beads are in the size range of approximately 10 nm to 1 mm, often being in a range from 50 nm to 1,000,000 nm, more preferably in a size range of approximately 100 nm to 0.1 mm, ideally being in a range from 1–10 micrometer, and can be manipulated using normal solution techniques when suspended in a solution.

Discrete emission spectra can be encoded into these materials by varying the amounts and ratios of different semiconductor nanocrystals, either the size distribution of semiconductor nanocrystals, the composition of the semiconductor nanocrystals, or other property of the semiconductor nanocrystals that yields a distinguishable emission spectrum, which are embedded into, attached to or otherwise associated with the material.

The semiconductor nanocrystals of the invention can be associated with the material by adsorption, absorption, covalent attachment, by co-polymerization or the like. The semiconductor nanocrystals have absorption and emission spectra that depend on their size and composition. These semiconductor nanocrystals can be prepared as described in Murray et. al., (1993) *J. Am. Chem. Soc.* 115:8706–8715; Guzelian et. al., (1996) *J. Phys. Chem.* 100;7212–7219; or International Publication No. WO 99/26299 (inventors Bawendi et al.). The semiconductor nanocrystals can be made further luminescent through overcoating procedures as described in Danek et. al., (1966) *Chem. Mat.* 8(1):173–180; Hines et. al., (1996) *J. Phys. Chem.* 100:468–471; Peng et. al., (1997) *J. Am. Chem. Soc.* 119:7019–7029; or Daboussi et. al., (1997) *J. Phys. Chem.-B,* 101:9463–9475.

The desired spectral emission properties may be obtained by mixing semiconductor nanocrystals of different sizes and/or compositions in a fixed amount and ratio to obtain the desired spectrum. The spectral emission of this staining solution can be determined prior to treatment of the material therewith. Subsequent treatment of the material (through covalent attachment, co-polymerization, passive absorption, swelling and contraction, or the like) with the staining solution results in a material having the designed spectral emission property. These spectra may be different under different excitation sources. Accordingly, it is preferred that the light source used for the encoding procedure be as similar as possible (preferably of the same wavelength and/or intensity) to the light source that will be used for the decoding. The light source may be related in a quantitative manner, so that the emission spectrum of the final material may be deduced from the spectrum of the staining solution.

A number of semiconductor nanocrystal solutions can be prepared, each having a distinct distribution of sizes and compositions, and consequently a distinct emission spectrum, to achieve a desired emission spectrum. These solutions may be mixed in fixed proportions to arrive at a spectrum having the predetermined ratios and intensities of emission from the distinct semiconductor nanocrystals suspended in that solution. Upon exposure of this solution to a light source, the emission spectrum can be measured by techniques that are well established in the art. If the spectrum is not the desired spectrum, then more of a selected semiconductor nanocrystal solution can be added to achieve the desired spectrum and the solution titrated to have the correct emission spectrum. These solutions may be colloidal solutions of semiconductor nanocrystals dispersed in a solvent, or they may be pre-polymeric colloidal solutions, which can be polymerized to form a matrix with semiconductor nanocrystals contained within. While ratios of the quantities of constituent solutions and the final spectrum intensities need not be the same, it will often be possible to derive the final spectra from the quantities (and/or the quantities from the desired spectra.)

The solution luminescence will often be adjusted to have the desired intensities and ratios under the exact excitation source that will be used for the decoding. The spectrum may also be prepared to have an intensity and ratio among the various wavelengths that are known to produce materials having the desired spectrum under a particular excitation source. A multichannel auto-pipettor connected to a feedback circuit can be used to prepare a semiconductor nanocrystal solution having the desired spectral characteristics, as described above. If the several channels of the titrator/pipettor are charged or loaded with several unique solutions of semiconductor nanocrystals, each having a unique excitation and emission spectrum, then these can be combined stepwise through addition of the stock solutions. In between additions, the spectrum may be obtained by exposing the solution to a light source capable of causing the semiconductor nanocrystals to emit, preferably the same light source that will be used to decode the spectra of the encoded materials. The spectrum obtained from such intermediate measurements may be judged by a computer based on the desired spectrum. If the solution luminescence is lacking in one particular semiconductor nanocrystal emission spectrum, stock solution containing that semiconductor nanocrystal may be added in sufficient amount to bring the emission spectrum to the desired level. This procedure can be carried out for all different semiconductor nanocrystals simultaneously, or it may be carried out sequentially.

Once the staining solution has been prepared, it can be used to incorporate a unique luminescence spectrum into the materials of this invention. If the method of incorporation of the semiconductor nanocrystals into the materials is absorption or adsorption, then the solvent that is used for the staining solution may be one that is suitable for swelling the materials. Such solvents are commonly from the group of solvents including dichloromethane, chloroform, dimethylformamide, tetrahydrofuran and the like. These can be mixed with a more polar solvent, for example methanol or ethanol, to control the degree and rate of incorporation of the staining solution into the material. When the material is added to the staining solution, the material will swell, thereby causing the material to incorporate a plurality of semiconductor nanocrystals in the relative proportions that are present in the staining solution. In some embodiments, the semiconductor nanocrystals may be incorporated in a different but predictable proportion. When a more polar solvent is added, after removal of the staining solution from the material, material shrinks, or unswells, thereby trapping the semiconductor nanocrystals in the material. Alternatively, semiconductor nanocrystals can be trapped by evaporation of the swelling solvent from the material. After rinsing with a solvent in which the semiconductor nanocrystals are soluble, yet that does not swell the material, the semiconductor nanocrystals are trapped in the material, and may not be rinsed out through the use of a non-swelling, non-polar solvent. Such a non-swelling, non-polar solvent is typically hexane or toluene. The materials can be separated and then exposed to a variety of solvents without a change in the emission spectrum under the light source. When the material used is a polymer bead, the material can be separated from the rinsing solvent by centrifugation or evaporation or both, and can be redispersed into aqueous solvents and buffers through the use of detergents in the suspending buffer, as is well known in the art.

The above procedure can be carried out in sequential steps as well. A first staining solution can be used to stain the materials with one population of semiconductor nanocrystals. A second population of semiconductor nanocrystals can be prepared in a second staining solution, and the material exposed to this second staining solution to associate the semiconductor nanocrystals of the second population with the material. These steps can be repeated until the desired spectral properties are obtained from the material when excited by a light source, optionally using feedback from measurements of the interim spectra generated by the partially stained bead material to adjust the process.

The semiconductor nanocrystals can be attached to the material by covalent attachment, and/or by entrapment in pores of the swelled beads. For instance, semiconductor nanocrystals are prepared by a number of techniques that result in reactive groups on the surface of the semiconductor nanocrystal. See, e.g., Bruchez et. al., (1998) *Science* 281:2013–2016; and Ghan et. al., (1998) *Science* 281:2016–2018, Golvin et. al., (1992) *J. Am. Chem. Soc.* 114:5221–5230; Katari et. al. (1994) *J. Phys. Chem.* 98:4109–4117; Steigerwald et. al. (1987) *J. Am. Chem. Soc.* 110:3046. The reactive groups present on the surface of the semiconductor nanocrystals can be coupled to reactive groups present on the surface of the material. For instance, semiconductor nanocrystals which have carboxylate groups present on their surface can be coupled to beads with amine groups using a carbo-diimide activation step, or a variety of other methods well known in the art of attaching molecules and biological substances to bead surfaces. In this case, the relative amounts of the different semiconductor nanocrystals can be used to control the relative intensities, while the absolute intensities can be controlled by adjusting the reaction time to control the number of reacted sites in total. After the bead materials are stained with the semiconductor nanocrystals, the materials are optionally rinsed to wash away unreacted semiconductor nanocrystals.

Referring once again to FIG. 1, labeled elements 12a, 12b (here in the form of semiconductor nanocrystal probes) may be useful in assays in a wide variety of forms. Utility of the probes for assays benefits significantly from the use of moieties or affinity molecules, which may optionally be supported directly by a label marker of the label, by the probe body matrix, or the like. Suitable moieties can have selective affinity for an associated detectable substance. The probes may, but need not necessarily, also include an integrated assay marker. In some embodiments, the assay marker will instead be coupled to the probes by coupling of a detectable substance to a moiety of the probe. In other words, the assay marker may (at least initially) be coupled to the detectable substance, typically by binding of a dye molecule, incorporation of a radioactive isotope or a different colored semiconductor nanocrystal, or the like. In other assays, the assay results may be determined by the presence or absence of the probe or bead (for example, by washing away probes having an unattached moiety) so that no dedicated assay marker need be provided.

In alternative embodiments, the material used to make the codes does not need to be semiconductor nanocrystals. For example, any fluorescent material or combination of fluorescent materials that can be finely tuned throughout a spectral range and can be excited optically or by other means might be used. For organic dyes, this may be possible using a number of different dyes that are each spectrally distinct.

This bead preparation method can be used generically to identify identifiable substances, including cells and other biological matter, non-biological chemicals, molecules, objects, and the like. Pre-made mixtures of semiconductor nanocrystals, as described above, are attached to objects to render them subsequently identifiable. Many identical or similar objects can be coded simultaneously, for example, by attaching the same semiconductor nanocrystal mixture to a batch of microspheres using a variety of chemistries known in the art. Alternatively, codes may be attached to objects individually, depending on the objects being coded. In this case, the codes do not have to be pre-mixed and may be mixed during application of the code, for example using an inkjet printing system to deliver each species of semiconductor nanocrystals to the object. The use of semiconductor nanocrystal probes in chemical and/or biological assays is more fully described in International Publication No. WO/0055631, the full disclosure of which is incorporated herein by reference.

The semiconductor nanocrystal probes may also be utilized to detect the occurrence of an event. This event, for example, may cause the source from which energy is transferred to assay marker 38 to be located spatially proximal to the semiconductor nanocrystal probe. Hence, the excitation energy from energy source 20 may be transferred either directly to assay markers 38, 38', or indirectly via excitation of one or more energy sources adjacent the semiconductor nanocrystal probes due to bonding of the test substances 35 to the moiety 35'. For example, a laser beam may be used to excite a proximal source such as a semiconductor nanocrystal probe 38' attached to one of the test substances 35 (to which the affinity molecule selectively attaches), and the energy emitted by this semiconductor nanocrystal 38' may then excite an assay marker 38 affixed to the probe matrix. Still further alternatives are possible. For example, any of the many assays in which the presence of an analyte causes a detectable label to bind to a moiety may be employed in the present invention so that binding of an assay marker binds to a bead indicates the presence of an analyte of interest.

Reading Beads

Referring once again to FIG. 1, energy source 20 generally directs excitation energy 22 in such a form as to induce emission of the spectral code from labeled element 12a. In one embodiment, energy source 20 comprises a source of light, the light preferably having a wavelength shorter than that of the spectral code. Energy source 20 may comprise a source of blue or ultraviolet light, optionally comprising a broad band ultraviolet light source such a deuterium lamp, optionally with a filter. Alternatively, energy source 20 may comprise an Xe or Hg UV lamp, or a white light source such as a xenon lamp, a Hg lamp, or a deuterium lamp, preferably with a short pass or bandpass filter UV filter disposed along the excitation energy path from the lamp to the labeled element 12 so as to limit the excitation energy to the desired wavelengths. Still further alternative excitation energy sources include any of a number of continuous wave (cw) gas lasers, including (but not limited to) any of the argon ion laser lines (457 nm, 488 nm, 514 nm, etc.), a HeCd laser, a solid-state diode laser (preferably having a blue or ultraviolet output such as a GaN based laser, a GaAs based laser with frequency doubling, a frequency doubled or tripled output of a YAG or YLF based laser, or the like), any of the pulsed lasers with an output in the blue or ultraviolet ranges, light emitting diodes, or the like.

The excitation energy 22 from energy source 20 will induce labeled element 12a to emit identifiable energy 24 having the spectral code, with the spectral code preferably comprising signals having relatively narrow peaks so as to define a series of distinguishable peak wavelengths and associated intensities. The peaks will typically have a half width of about 100 nm or less, preferably of 70 nm or less, more preferably 50 nm or less, and ideally 30 nm or less. In many embodiments, a plurality of separate signals will be included in the spectral code as sensed by sensor 18. As semiconductor nanocrystals are particularly well-suited for generating luminescent signals, identifiable energy 24 from label 12a will often comprise light energy. To help interpret the spectral code from the identifiable energy 24, the light energy may pass through one or more monochromator. A Charge-Coupled Device (CCD) camera or some other two-dimensional detector or sensor 18 can sense and/or record the images for later analysis. In other embodiments, a scanning system may be employed, in which the labeled element to be identified is scanned with respect to a microscope objective, with the luminescence put through a single monochromator or a grating or prism to spectrally resolve the colors. The detector can be a diode array that records the colors that are emitted at a particular spatial position, a two-dimensional CCD, or the like. Alternatively, the spectral code can be read by imaging the identifiable items through a series of bandpass filters and measuring the signals at each wavelength.

Figure 1A:
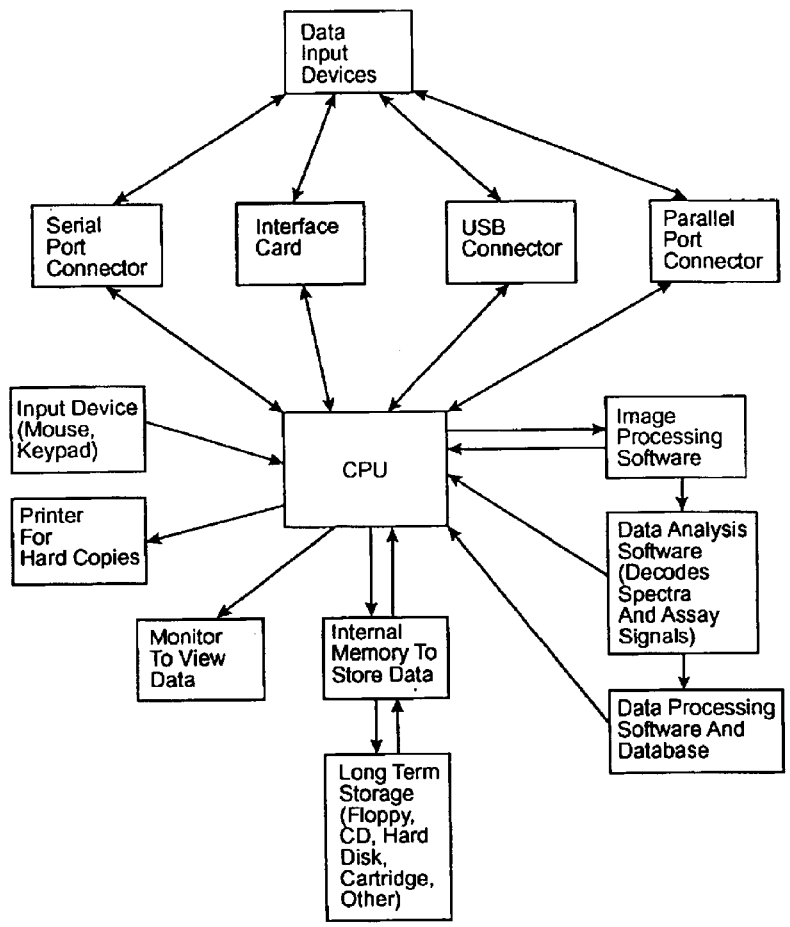
FIG. 1A schematically illustrates an exemplary processor for the system of claim 1.

Information regarding these spectra from the labeled elements 12 will generally be transmitted from sensor 18 to processor 16, the processor typically comprising a general purpose computer. Processor 16 will typically include a central processing unit, ideally having a processing capability at least equivalent to a Pentium I® processor, although simpler systems might use processing capabilities of a Palm® handheld processor or more. Processor 16 will generally have input and output capabilities and associated peripheral components, including an output device such as a monitor, an input such as a keyboard, mouse, and/or the like, and will often have a networking connection such as an Ethernet, an Intranet, an Internet, and/or the like. An exemplary processing block diagram is schematically illustrated in FIG. 1A.

Processor 16 will often make use of a tangible media 30 having a machine-readable code embodying method steps according to one or more methods of the present invention. A database 32, similarly embodied on a machine-readable code, will often include a listing of the elements included in library 8, the spectral codes of the labels associated with the elements, and a correlation between specific library elements and their associated codes. Processor 16 uses the information from database 32 together with the spectrum characteristics sensed by sensor 18 to identify a particular library element 12a. The machine-readable code of program instructions 30 and database 32 may take a wide variety of forms, including floppy disks, optical discs (such as CDs, DVDs, rewritable CDs, and the like), alternative magnetic recording media (such as tapes, hard drives, and the like), volatile and/or non-volatile memories, software, hardware, firmware, or the like.

As illustrated in FIG. 1, methods for detecting and classifying spectral labels (such as encoded materials and beads) may comprise exposing the labels to light of an excitation source so that the semiconductor nanocrystals of the label are sufficiently excited to emit light. This excitation source is preferably of an energy capable of exciting the semiconductor nanocrystals to emit light and may be of higher energy (and hence, shorter wavelength) than the shortest emission wavelength of the semiconductor nanocrystals in the label. Alternatively the excitation source can emit light of longer wavelength if it is capable of exciting some of the semiconductor nanocrystals disposed in the matrix to emit light, such as using two-photon excitation. This excitation source is preferably chosen to excite a sufficient number of different populations of semiconductor nanocrystals to allow unique identification of the encoded materials. For example, using materials stained in a 1:2 ratio of red to blue and a 1:3 ratio of red to blue, it may not be sufficient to only excite the red emitting semiconductor nanocrystals (e.g., by using green or yellow light) of the sample in order to resolve these beads. It would be desirable to use a light source with components that are capable of exciting the blue emitting and the red emitting semiconductor nanocrystals simultaneously, (e.g., violet or ultraviolet). There may be one or more light sources used to excite the populations of the different semiconductor nanocrystals simultaneously or sequentially, but each light source may selectively excite sub-populations of semiconductor nanocrystals that emit at lower energy than the light source (to a greater degree than higher energy emitting sub-populations), due to the absorbance spectra of the semiconductor nanocrystals. Ideally, a single excitation energy source will be sufficient to induce the labels to emit identifiable spectra.

One potential practical problem with existing encoding schemes is that to read precise spectral codes, it is beneficial to dye the beads precisely. Since intensity is one of the parameters for current spectral coding systems, the beads should be uniformly and reproducibly dyed. It is also important that no degradation in quantum yield results over time, especially if degradation is not uniform between different colored fluorophores. While these problems are not an issue in theoretical coding systems, in practice this may result in severe physical limitations. Finally, in order to get a large number of possible codes using the currently available techniques, different signals or color channels may be placed spectrally very close to each other. Thus, the individual signals are highly overlapping, creating a technological difficulty in reading the codes, especially if there is some uncertainty or degradation in the intensity of each channel.

It would be valuable to have a spectral coding system that does not require the precise deconvolution of highly overlapping emission spectra, and/or does not require the precise distinction between many different peak intensities, especially in highly overlapping spectra. The current invention provides a spectral coding system that optionally uses only substantially separated spectral peaks without excessive spectral overlap, and often does not require stringent intensity regulation of the peaks. This method allows for approximately 100,000 to 10,000,000 or more unique codes. Surprisingly, maintaining sufficient wavelength separation between signals included in a code can actually enhance the robustness of the code and/or the amount of information which can be transmitted by the code.

Spectral Codes

This invention takes advantage of the fact that it is possible to fabricate semiconductor nanocrystals with very precise emission wavelengths that are tunable almost continuously over the available spectrum for each material. Nanocrystals with wavelengths that are tunable in approximately 1 nm steps can be prepared. While it may be necessary to separate two overlapping spectral peaks by many nanometers to distinguish them easily, it is straightforward to identify the wavelength of a single non-overlapping peak within 1 nm. Hence, the information which can be effectively communicated by a spectral code is enhanced by maintaining a minimum spectral separation between the signals of the spectra, as the wavelengths of the separated peaks can be accurately identified. In other words, by separating signals within dedicated wavelength ranges, the peak wavelengths of each signal can be identified from among more tightly spaced predetermined allowable wavelengths within each range.

To understand the advantages of signal separation within a spectral code, it is helpful to review a simple spectral code in which only a single peak 40 is used. In the case of a single-peak spectral code, each signal wavelength is a different code (see FIGS. 1B–D). When fabricated with CdSe, for example, a semiconductor nanocrystal with a spectral range of approximately 490–640 nm, can be used to generate about 150 single-peak codes, with allowable wavelengths being separated by only 1 nm. Although interpretation of codes having multiple overlapping signals separated by only 1 nm might be quite challenging, the use of a single isolated signal within this simple code avoids this problem, allowing relatively simple identification of the isolated peaks without having to resort to complex (and possibly error-prone) overlapping signal deconvolution.

While the single-peak coding system is limited in the number of potential codes, it is less sensitive to differences in single-code or code-to-code signal intensity. This robustness of the single peak code is in part a result of our ability to accurately measure the peak wavelength regardless of the intensity, as long as the peak is observable above the background noise. This code is also insensitive to degradation of quantum yield over time. Furthermore, the code is insensitive to the size distribution of each nanocrystal sample since the peak wavelength can be determined regardless of the peak width (expressed as full width at half maximum peak height or "FWHM"), assuming that the object(s) being coded are uniformly attached to the nanocrystals (and/or the nanocrystals are uniformly attached to the object or objects). Finally, this code is easy to read, since the fitting of a single Gaussian peak with no deconvolution of overlapping peaks is quite straightforward.

Figure 1B:
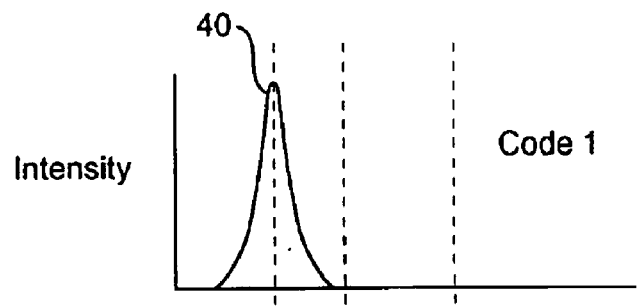
FIGS. 1B, 1C, and 1D schematically illustrate a simple single-signal spectral code.
Figure 1C:
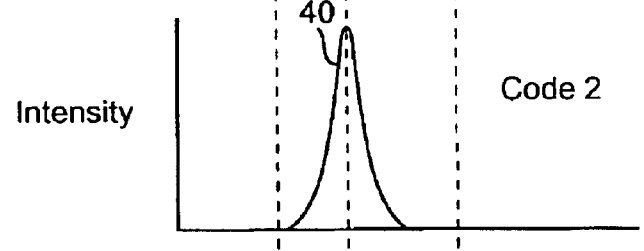
Figure 1D:
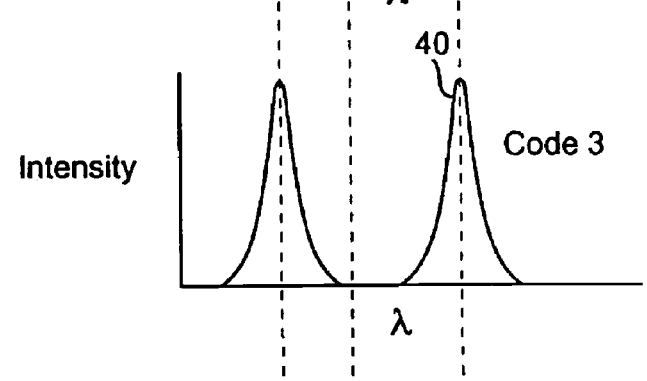
Figure 2A:
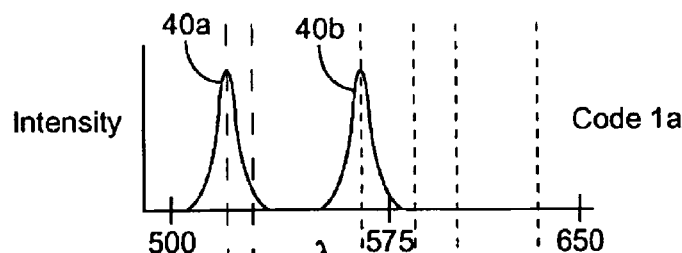
FIGS. 2A–E schematically illustrate a spectral code having a plurality of signals.
Figure 2B:
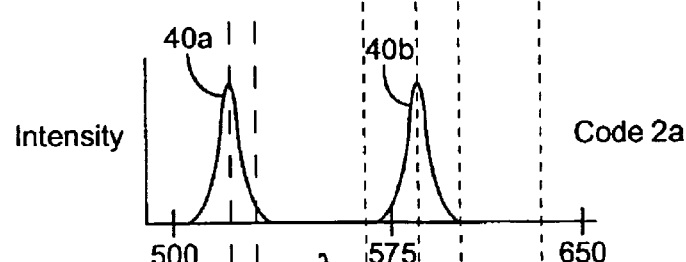
Figure 2C:
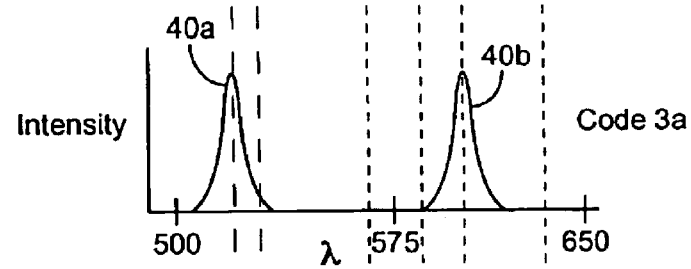
Figure 2D:
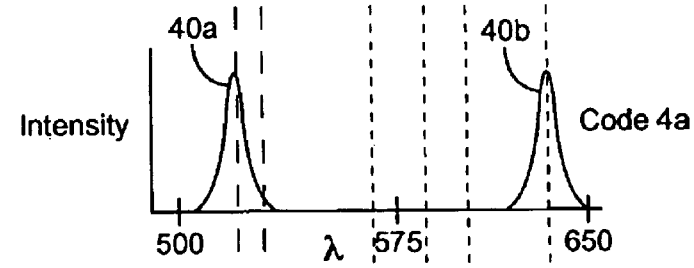
Figure 2E:
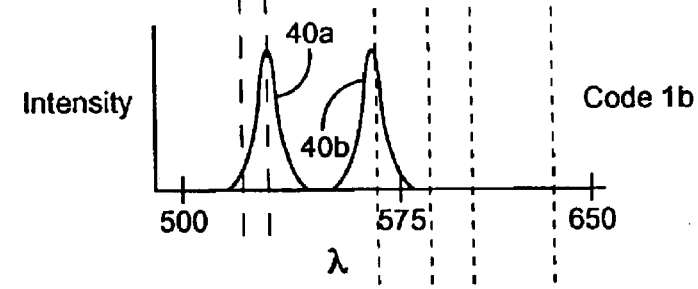

The single peak binary coding system of FIGS. 1B–D not only eases the requirements for bead dying and semiconductor nanocrystal sample quality and sample degradation, it also eases the requirements on the excitation source. For example, while all semiconductor nanocrystals can be excited with a single excitation source, they may not be excited equally. A 488 nm excitation light may excite 600 nm semiconductor nanocrystals more efficiently than 500 nm nanocrystals. Codes relying on intensities often use different concentrations of semiconductor nanocrystals to normalize for the size-dependent cross-sections. However, if a code is developed using a given excitation wavelength, it should be read using that specific wavelength, since the relative extinction coefficient for each size nanocrystal may be significantly different at other excitation wavelengths. Thus, for every different light source, a different set of codes might be developed. In addition, if a lamp source is used, degradation of the lamp can result in changes in the excitation source, thereby compromising the codes. The relative intensity insensitivity of the coding system described herein can decrease such problems.

Referring now to FIGS. 2A–E, many of the advantages of a single-peak system can be provided for multiple peak systems by maintaining a minimum wavelength separation between adjacent peaks 40a, 40b within each code. Using two peaks rather than one increases the number of potential codes. To retain the robust characteristics of the one-peak code, a two-peak code can limit the allowable codes to those having sufficient separation between the two peaks 40a, 40b to prevent excessive signal overlap within the spectral codes. As can be understood with reference to FIG. 3, each peak may still occupy any of the quite tightly spaced discrete wavelengths of our single-peak code, with the exception of those which are excessively near the other peak.

Figure 4:
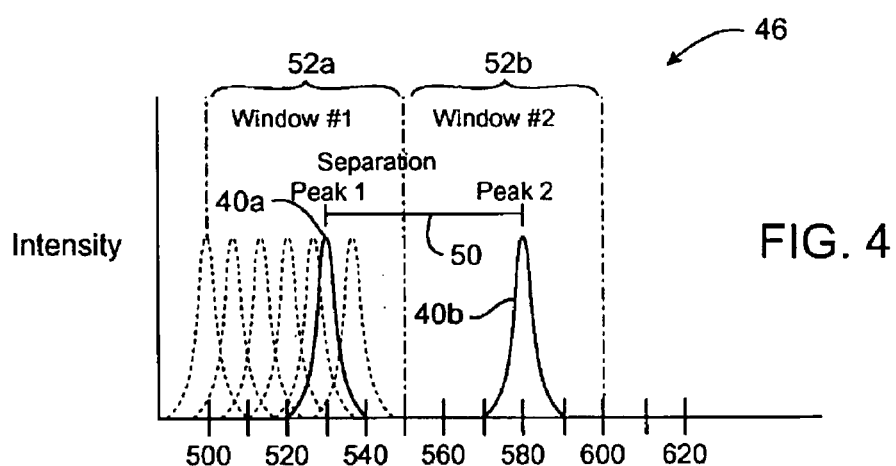
FIG. 4 graphically illustrates rules used to establish a series of spectral codes so that the signals are sufficiently separated to allow tighter candidate discrete peak wavelengths.

Referring now to FIG. 4, as an example of a two-peak code, we can assume that each peak is chosen to reside within a 75 nm wavelength range, (e.g., peak 1 is tuned from 490–565 nm and peak 2 is tuned from 575–650 nm). These wavelength ranges are sometimes referred to herein as "windows". The wavelength of each peak can again be varied within its associated window in small steps to create a myriad of codes. Using 1 nm steps and a minimum peak separation of about 75 nm, this coding system produces approximately 3000 distinct codes. The system can be expanded to include many peaks, the minimum separation between peaks preferably being sufficient to allow precise determination of the peak wavelength of each.

Figure 3:
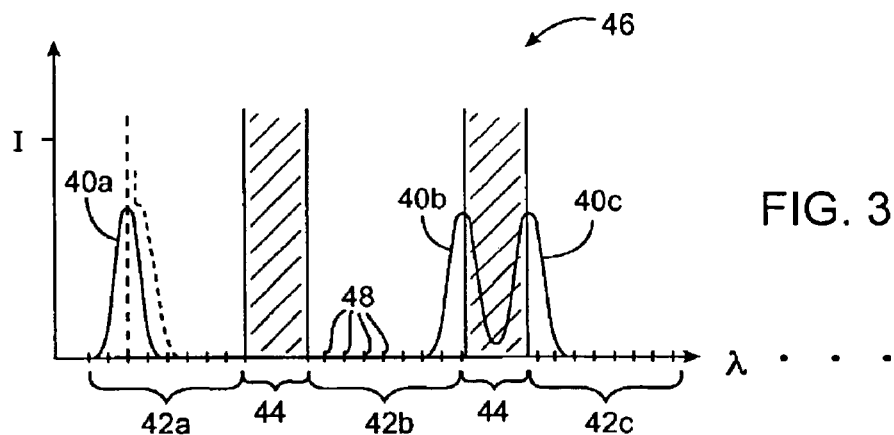
FIG. 3 schematically illustrates a spectral code having a single signal within each of a plurality of separated windows.

With reference to FIGS. 3 and 4, peak-to-peak separation may be imposed using predetermined separated windows, and/or by determining appropriate windows based on the signals within a spectral code. As can be understood with reference to FIG. 3., predetermined wavelength ranges or windows 42a, 42b, 42c, . . . (generically referred to as predetermined windows 42) each have a single associated signal with a wavelength peak 40a, 40b, 40c, . . . respectively, disposed within the associated predetermined window. As mentioned above, predetermined wavelength intervals 48 within each window can then be quite close, so that if two signals had wavelength peaks at adjacent intervals, the signals could overlap sufficiently to mask the peak wavelengths, as shown in phantom in predetermined window 42a. A signal wavelength separation 44 may be disposed between each pair of adjacent predetermined windows 42, and the spectral code will preferably not have a signal with a peak disposed in the separations at sufficient intensity to mask an adjacent signal wavelength. As only a single peak is generally present within each window, and as the separations ensure a minimum spacing between adjacent peaks in different windows (see peaks 40b and 40c in FIG. 3), spectral deconvolution techniques may optionally be avoided despite the tight spacing of the wavelength intervals 48, and/or the discrete wavelength intervals can be decreased while maintaining reliability of the code. Predetermined windows 42 may optionally be common to some or all of the spectral codes of a library. This can facilitate accurate reading of the code, as the code reading hardware and software need only identify no more than a single peak wavelength within each predetermined window. Optionally, the system may also determine if there is an absence of a signal in one or more of the predetermined windows.

As can be understood with reference to FIG. 4, peak-to-peak signal separation 50 may alternatively be maintained by limiting the signals of each code of a library to selected wavelength increments based on the wavelengths of other signals of the code. Such a windowing system may be determined as each code is created and/or interpreted using a minimum separation rule, often in combination with established or predetermined discrete wavelength increments. The resulting acceptable codes may also have a single wavelength peak 40 disposed within an associated window 52a, 52b . . . (generically, windows 52), and the size of the windows and/or the acceptable discrete wavelengths within each window may vary within the spectral code 46 depending on the locations of the peaks within adjacent windows so as to maintain the minimum separation.

Regardless of whether the windows are predetermined, common to some or all of the codes of the library, and/or derived from separation rules for each signal of each code, the peak-to-peak signal wavelength separation will generally be at least 5 nm, often being at least 15 nm, preferably being at least 30 nm, and in many cases being 50 nm or more. Such spacings facilitate the use of small discrete wavelength increments within the windows, with the increments typically being 10 nm or less, often being 5 nm or less, in many cases being 2 nm or less. Information-dense codes may benefit from increments of 1 nm or less, optionally being less than 1 nm. Within each window, codes will generally have a plurality of signal wavelength increments, typically being 5 or more wavelength increments, optionally being 10 or more wavelength increments. The spectra of some or all of the codes of a library will often have a plurality of signals, with each signal defining a wavelength, typically as a peak wavelength of a discrete signal, although other wavelengths defined by the signal are also possible.

As an example of the power of this type of system, the following is a relatively conservative example of a potential code using realistic parameters. The variables for this example are as follows: (1) spectral bandwidth is 300 nm; (2) coding-peak resolution, i.e., the minimum step size for identifying an isolated peak within a single channel, is 4 nm; (3) minimum spacing between peaks is 50 nm; and (4) the maximum number of peaks in each code is 6. In this case, the number of potential codes is approximately 200,000. This assumes a purely binary code, in which the peak within each channel is either "on" or "off". By adding a second intensity, i.e., wherein intensity is 0, 1 or 2, the number of potential codes increases to approximately 5 million. If the coding-peak resolution is reduced to 1 nm, the number of codes increases to approximately $1 \times 10^{10}$.

Figure 5:
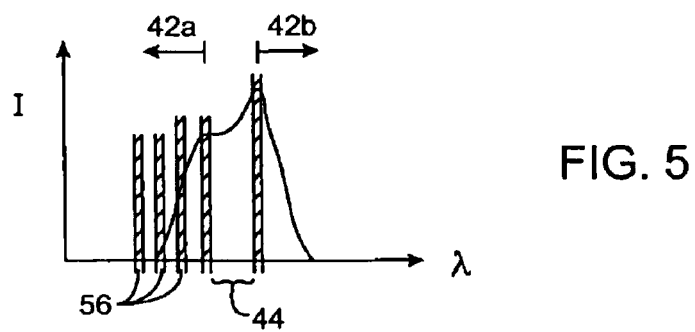
FIG. 5 illustrates one method for spectral deconvolution which may be used to interpret binary and/or higher order codes according the principles of the present invention.

For a binary code, the production requirements for dying levels, photostability, and size distribution are virtually eliminated. The addition of two intensities only marginally increases these requirements. Generally, spectral codes having a limited number of intensities and separated peaks are easier to read than codes employing overlapping peaks of many different intensities, since it is easier to read precisely the wavelength of the separated peaks. Nonetheless, as can be understood with reference to FIG. 5, the signal separations techniques of the present invention may find use within coding schemes having significant overlapping of adjacent peaks. By combining a separated-signal code with known spectral deconvolution methods (such as measuring intensities adjacent the discrete wavelengths using bandpass filters 56, and using standard matrix deconvolution methods to determine individual signal intensities and wavelengths), a relatively robust and information-dense code may be established which allow a user to identify a variety of different intensities despite overlap between adjacent signals.

The calculations above may be based on the following model, which is again illustrated in FIG. 4. If a code has at most two peaks, with a minimum allowable separation of 50 nm, and the possibility of tuning each peak is here assumed to be in steps of 5 nm, the system can be modeled as being two-peak, each peak residing within adjacent 50 nm spectral windows. When peak-2 is at 590 nm, peak-1 can be at any wavelength between 500–540 nm and meet the requirement that the peaks are at least 50 nm apart. If peak-2 is at 585 nm, then peak-i can be between from 500–535 nm, and the like. As described, this produces 55 distinct codes. Added to the combination of two peak codes are also additional codes that have only a single peak, yielding a total of 75 codes. Codes with N peaks are generated in a similar way, counting all possible codes involving N, N-1, N-2 . . . 1 peaks.

Valid codes can be generated using an algorithm that evaluates all possible codes. Potential codes are represented as a binary code, with the number of digits in the code corresponding to the total number of colors. For example, a 16-bit code could represent 16 colors of semiconductor nanocrystals from 500 nm to 575 nm, at 5 nm spacing. A binary code 1000 0000 0000 0001 represents the presence of the 500 nm and 575 nm peaks. Each of these 16-bit numbers can be evaluated for validity, depending on the spacing that is required between adjacent peaks, for example 001 0 0100 0000 0000 is a valid code if peaks spaced by 15 nm or greater can be recognized, but is not valid if the minimum spacing between adjacent peaks is, for example, 20 nm. Using a 16-color code, as described above with 500 to 575 nm range and 5 nm spacing between colors, the different number of possible codes can be calculated using a simple algorithm (see Table 1), in which the number of codes versus minimum spectral spacing between adjacent peaks is displayed.

TABLE 1

The number of unique codes with a binary 16-color system.

| Spectral Separation | 5 nm | 10 nm | 15 nm | 20 nm | 25 nm | 30 nm |
|---|---|---|---|---|---|---|
| Number of unique codes | 65535 | 2583 | 594 | 249 | 139 | 91 |

If different intensities can be discerned within each color, then the number of codes can be increased dramatically. For example, using the 16-color code above, with 15 nm minimum spacing between adjacent peaks in a code, 7,372 different codes are possible if two discrete intensities, i.e., a ternary system, can be discerned for each color, and 38,154 for a quaternary system, i.e., wherein three discrete "on" intensities can be discerned.

If a simple combinatorial coding scheme had been used, with six colors spaced at 15 nm intervals using slightly more spectral range than above, then 64 codes would be possible with binary coding, 729 with base three coding, and 4096 with base four coding, compared with 594, 7392, and 38154, respectively.

In a preferred embodiment, this spectral coding system is created using polymer beads impregnated with semiconductor nanocrystals, as described above. Different size and/or composition nanocrystals are added to the beads in roughly equal amounts to create each code. The codes are then read by exciting with short wavelength optical excitation or any other suitable form of excitation, and the emission code is read either using a spectrometer or other device capable of high spectral resolution.

In an alternative embodiment, the material used to make the codes does not need to be semiconductor nanocrystals, but can be any material or combination of materials that can generate signals which can be finely tuned throughout a spectral range and can be excited optically or by other means. For organic dyes, this may be possible using a number of different dyes that are each spectrally distinct. The material used to make the codes may also comprise a mixture of semiconductor nanocrystals and other markers, for example, a mixture of semiconductor nanocrystals and organic dyes.

This method can be used generically to identify objects. Pre-made mixtures of semiconductor nanocrystals, as described above, are attached to objects to render them subsequently identifiable. Many identical or similar objects can be coded simultaneously, for example, by attaching the same semiconductor nanocrystal mixture to a batch of microspheres using a variety of chemistries known in the art.

Alternatively, codes may be attached to objects individually, depending on the object being coded. In this case, the codes do not have to be pre-mixed and may be mixed during application of the code, for example using an inkjet printing system to deliver each species of semiconductor nanocrystal to the object.

Spectral Process Coding

Window-based coding schemes will have useful applications in, for example, recording the process that an object or element has gone through. One or more selected semiconductor nanocrystal species from within a window can be added at a given process step, with the added semiconductor nanocrystals representing the particular process that has been carried out on the object. By limiting the selection of markers (and particularly, the signal peaks) added at a given step to a predetermined and/or rule-derived window, and by limiting any other separate process steps to markers with signals in separate windows, the spectral code indicating each process step can be readily and individually interpreted without spatially resolving the markers. In other words, a plurality of codes can be read simultaneously and individually interpreted.

One example of a use for spectrally separated codes is in the field of combinatorial synthesis. Split-and-pool methods are often used in combinatorial synthesis to perform sequentially different monomer additions. In this application, separate spectral windows can be designated for each synthesis stage, for example, with six synthesis stages, 20 nm windows could be designated from 450–470 nm, 490–510 nm, 530–550 nm, 570–590 nm, 610–630 nm, 650–670 nm, thereby ensuring that adjacent peaks are at least 20 nm apart. If each synthesis stage has several different possible processes, then a semiconductor nanocrystal solution is added to the object to reflect the process that has just been carried out. In a six-stage reaction, there can be five different monomers added at each stage. In the first stage, addition of monomer-1 would also include addition of 450 nm semiconductor nanocrystals, monomer-2, 455 nm, monomer-3, 460 nm, monomer-4, 465 nm, monomer-5, 470 nm. In the second stage, monomer-1 is 490 nm, and so forth for each stage in the process. Following the process, the processing history of any object or element can be obtained by decoding the spectral code, (e.g., by reading the peaks in the emission spectrum and correlating them with the known processes carried out at each step). Similar codes might be established with more than one peak in each window (for example, to identify which of 2000 different test materials was added at a single step), with the different signals within each window optionally being disposed within separated sub-windows.

In light of the above, the wavelength separated signal code schemes described herein have advantages over existing schemes is their ease of implementation, ease of reading, and high information content.

Reference Signals

Figure 6A:
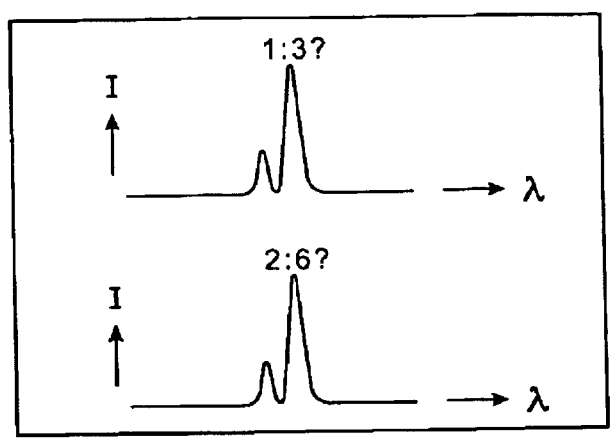
FIG. 6A schematically illustrates a potentially ambiguous multi-signal spectral code.

Referring once again to FIG. 1, the strength of the overall spectra sensed by sensor 18 can vary due to a large number of causes, including the distance between the label and sensor, orientation of the label bodies, ambient noise, and the like. Hence, reading an absolute intensity from labeled element 12a may be problematic. As a result, the absolute emission energy might be lost in the two-dimensional spectral image, potentially leading to ambiguity between different codes having similar wavelengths and intensity ratios, but different absolute intensities, as illustrated in FIG. 6A. As shown in this example, it may be difficult to properly distinguish between a first spectral code comprising red at an intensity value of 1 and blue at an intensity value of 3, and a second distinct code with similar colors but having intensities of 2 (red) and 6 (blue). Accurate identification of specific (and often discrete) absolute wavelengths may pose similar challenges, particularly when the allowable wavelength increments are tightly spaced and/or the spatial position of the label markers are not precisely controlled.

For spectrally encoded beads and other spectral labels, interpretation of the code can be facilitated if a calibration signal is included within the code. By including a reference marker to generate such a calibration signal (among the signal generating markers of the label) the reference signal from the reference marker can be compared to other signals of the code for calibration of discrete signal intensity ratios, to identify discrete signal wavelengths, and the like.

Spectral codes will generally be created using signals having different wavelengths (which may be referred to herein as code channels) and intensities. The calibration signal within the code may be referred to herein as the "reference channel." The intensity of each code channel will change in discrete amounts or unit steps, (e.g. intensity value 2 is twice intensity value 1 and 50% of the intensity value 4). As described above, however, fluctuations in manufacturing, sensing or experimental conditions, either static or dynamic, can make it difficult to determine the absolute intensity of the signals within a spectral code.

Figure 6B:
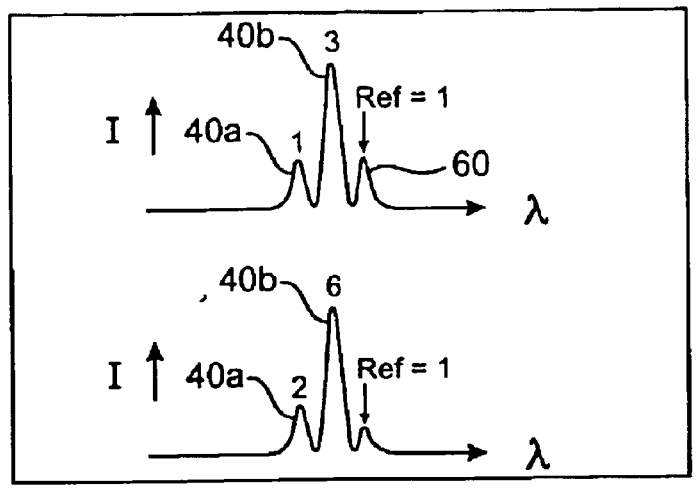
FIG. 6B schematically illustrates an unambiguous code having a calibration reference signal.
Figure 7:
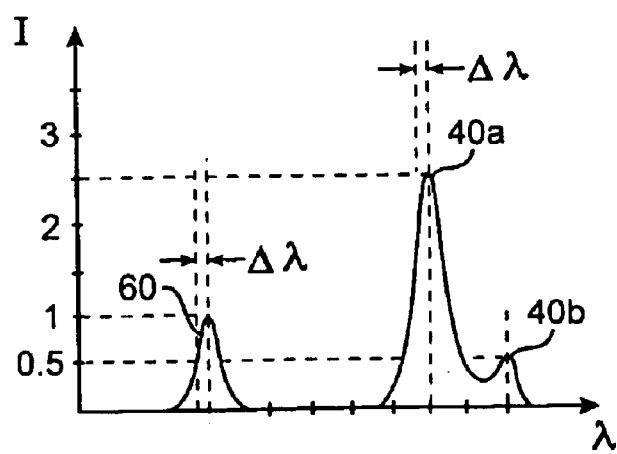
FIG. 7 illustrates calibration of an intensity and/or wavelength of a spectral code using a reference signal.

The presence of a calibration signal within a spectral code significantly facilitates code differentiation among otherwise ambiguous codes. Referring now to FIG. 6B, for example, a spectral code comprising red at an intensity value of 1 and blue at an intensity value of 3 may be readily distinguished from the second distinct code of 2 (red) and 6 (blue) by referencing the intensities of the signals to the intensity of a calibration peak 60 within each code. In a simple calibration scheme illustrated in FIG. 7, calibration peak 60 may always be deemed to have an intensity of (for example) 1, and all other intensities can be determined relative to that peak intensity from relative intensity ratios between the intensities of the other signals and the intensity of the reference signal. Note that the presence and strength of the reference signal may also provide a gauge of the quality of the spectra relative to, for example, the overall background noise. The intensity ratios may be limited to discrete ratios, such as integer multiples of the reference intensity (or some fraction thereof), or a wide variety of alternative intensity identification criteria might be established.

The reference channel is preferably chosen to be either the longest or shortest wavelength peak within the spectral code. Alternative reference signal standards may also be established, including the use of a highest or lowest intensity signal of a code, the use of a common reference wavelength for some or all of the codes of a library, the use of a middle wavelength between an equal number of longer and shorter wavelengths, and the like. By use of standard reference signal identification criteria, even where the absolute emission energy is lost in, for example, a two dimensional spectral image, it can be regained, since the absolute energy of the reference channel is known and the spectral code can be calibrated relative to the internal reference channel.

In addition to intensity calibration, the reference channel can serve as a wavelength calibration. Measured wavelengths may differ from absolute wavelengths for a variety of reasons, including measurement error, spatial inaccuracies, and the like. As can be understood with reference to FIG. 7, a known reference wavelength of reference peak 60 may be compared with a measured wavelength of the reference peak to determine a wavelength correction factor $\Delta\lambda$. This wavelength correction factor might be directly applied to other peak wavelengths, or more sophisticated wavelength correlations might be derived, for example, based on the geometry and/or other characteristics of the sensor.

Figure 8A:
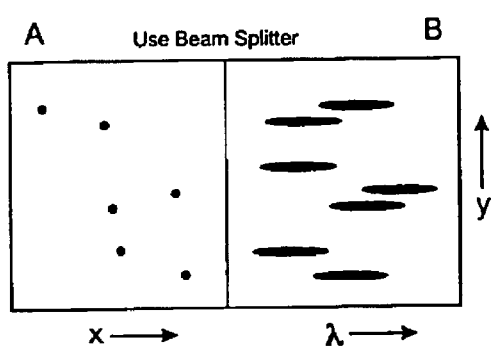
FIGS. 8A and 8B schematically illustrate two-dimensional imaging using a spectrometer to read a plurality of spectral codes with reference to a calibration reference signal.
Figure 8B:
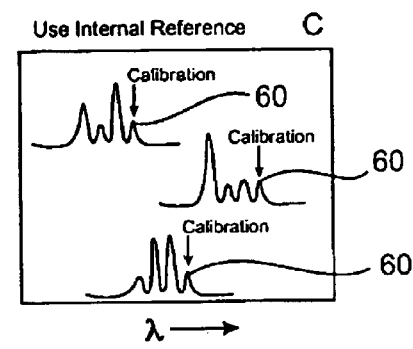

As can be understood with reference to FIGS. 8A and B, (and as more fully described in parent provisional application Serial No. 60/195,520, previously incorporated herein by reference), simultaneous identification from a plurality of spectrally labeled beads might be accomplished by obtaining a two-dimensional image with a modified linear spectrometer without an entrance slit and a two-dimensional detector. The discrete images from individual beads may define the spatial position of the spectra entering the spectrometer, with the spectral resolution of the system defined, in part, by the size of the discrete images or beads. Since the spatial position of the light from each point or bead varies across the x axis relative to the original slit opening, the calibration for each spectral code might be significantly different. Splitting the original image and passing one portion through a dispersive grating to create a separate image and spectra might help to avoid this calibration error, as the location of the bead might be determined at least in part from the separated image. Use of an internal calibration signal peak 60 within each spectral code may also help to avoid wavelength ambiguity.

The internal intensity reference can also be used as a reference for the quantity of analyte bound to the surface of each bead. In that way, a calibration standard can be provided for assays that use spectrally encoded beads. This invention will be useful in any application where spectrally encoded beads are used, including static and flow imaging applications, as well as non-imaging based detection systems. It will also be useful in any application where it is necessary or desirable to quantify the amount of analyte detected in an assay.

Spectral Code Creation

The present invention will often make use of semiconductor nanocrystals (or other structures) to, at least in part, define spectral codes. Uses for these codes including identifying cells, beads, or other microscopic objects, in addition to providing an "invisible" code on items like jewelry, watches, and other small or awkward items, and the like. Codes can optionally be created by using substantially non-overlapping colors of semiconductor nanocrystals, and then combining the nanocrystals in unique ratios, or according to absolute levels. Alternative codes might be created by relying on overlapping signal deconvolution.

The code creation methods described herein optionally use a computer program to combine or mix together, in silico (that is, using computer modeling), emission signals from semiconductor nanocrystals. These individual marker signal spectra can be real spectra from nanocrystals that have already been manufactured, or simulated spectra for nanocrystal batches that can be manufactured. Candidate code spectra are then compared against one another, with acceptable codes added to the library in order to create an optimal set of codes that are sufficiently different from each other to allow robust code assignment given constraints such as code-number requirements and instrument resolution. A further method uses stored patterns of known code spectra against which to evaluate an unknown spectrum, in order to assign a code to the unknown spectrum, or to declare it as "no match." To do this, several steps are performed, some optional: (1) creation of a code; (2) creation of a template for the code; (3) comparison of a sample spectrum against all possible templates; and (4) assignment of "match" or "no match" to the sample based upon its degree of similarity to one of the templates and/or dissimilarity to the remainder.

Coded objects can be created by attaching one or more semiconductor nanocrystal batches to an object or to many objects simultaneously. One criterion for creating useful codes is that, when a code is analyzed, it can be uniquely identified within the statistical confines of the experiment or actual code reading equipment. Generally, all codes to be used in a given application should be spectrally resolvable, i.e., sufficiently spectrally dissimilar within manufacturing tolerances and/or reading error, such that the rate of incorrect decoding is very low. The acceptable error rate depends on the application. Codes may be created randomly or systematically. Using the random approach, mixtures of semiconductor nanocrystals are created and then used as codes. Using the systematic approach, semiconductor nanocrystal batches are chosen, and mixed together in the appropriate ratios to generate the codes. In both approaches, the composite emission spectrum of each new code is compared to the emission spectrum of all other codes that will be used in the application. This can be done prior to the actual physical creation of the code, by using predicted spectra, or can be done by reading the spectrum of the new code prior to, or after, attaching the code to the object(s). If the code is non-overlapping, i.e., will not be misclassified when noise, aging, reader differences, or other factors are taken into account, then the code is valid to be used. The emission spectrum of the new code is stored digitally so that putative new codes, and unknown codes during code reading, can be compared against it. Preferably, reading accuracy will be incorporated into the comparison of prior codes with new codes, the reading accuracy generally being determined based on known properties of one or more of the excitation energy source, the sensor, and the data manipulation performed by the processor.

When many items are being coded with the same code, e.g., when attaching semiconductor nanocrystals to microspheres or beads in a batch mode, it is useful to analyze more than one of those objects and store an average, or representative, spectrum for the code. Once this has been done, the actual spectrum for each sample object can be compared with the average spectrum to ensure that they are correctly identified. They may also be compared against the spectra of other codes to ensure that they are not misidentified. Furthermore, statistical information regarding, for example, reproducibility and confidence levels can be gleaned at this stage.

The stored emission spectrum may herein be called the code's "template" and can have been generated experimentally by analyzing coded object(s) or semiconductor nanocrystal mixtures, or can be generated in silico by adding together emission spectra from the semiconductor nanocrystals that make up the code, along with any required correction factors.

Template emission spectra may be generated by using the instrument (or a similar instrument, or a computer model of the instrument) that will be used for reading the code, optionally correcting for any instrument-to-instrument variation. For example, for semiconductor nanocrystal-dyed microsphere assays it is desirable to analyze wells that contain a single or a few different known coded beads that have been processed through assay conditions. The template emission spectra may be generated for each encoded bead reader instrument so that during analysis, the templates for a given reader or assay are used.

Many different systematic methods for creating codes can be envisaged. For example, two colors of semiconductor nanocrystals may be used and the ratio of color 1:color-2 varied to create different codes. Using additional colors, the different ratios can be varied to create codes that are more complex.

Semiconductor nanocrystal batches that have the same color, i.e., the same peak wavelength, but have different peak widths, can be used to create two different codes if sufficient spectral data is gathered to allow these to be defined as being significantly different. These batches can also be mixed to create intermediate linewidths and hence more unique codes.

A computer-based method that uses all physically available semiconductor nanocrystal spectra, or that uses electronically generated spectra of all manufacturable semiconductor nanocrystal batches, can be used. In this case, the computer is programmed to combine systematically or randomly different amounts of these semiconductor nanocrystal spectra, in silico, along with any correction factors desired due to energy or electron transfer, emission intensity variations, or wavelength changes that may occur. The electronically created spectra are compared against current codes and any that are sufficiently distinguishable are candidates for manufacturing into real physical codes. This type of approach can also be used to create code sets, i.e., manufacturable emission spectra that are chosen to be maximally different from one another according to predetermined comparison criteria such as the residual value from a least squares fitting, or other methods known in the art.

Data on the overall emission spectrum of a code can be gathered by exciting the semiconductor nanocrystals with an appropriate source, e.g., laser, lamp, light-emitting diode, or the like, and reading the emitted light with a device that provides spectral information for the object, e.g., grating spectrometer, prism spectrometer, imaging spectrometer, or the like, or use of interference (bandpass) filters. Using a two-dimensional area imager such as a CCD camera, many objects may be imaged simultaneously. Spectral information can be generated by collecting more than one image via different bandpass, longpass, or shortpass filters (interference filters, colored glass filters, or electronically tunable filters are appropriate). More than one imager may be used to gather data simultaneously through dedicated filters, or the filter may be changed in front of a single imager. Once this data has been gathered, it can be processed to generate spectral information about objects in the image, or for each pixel, or group of pixels in the image, via straightforward image processing techniques.

The emission spectrum from the sample object is compared against all the known templates. This can be done using many techniques known in the art such as least squares fitting, Fourier analysis, Kolmogorov-Smirnov Test, Pearson Rank Correlation test, or the like (see *Numerical Recipes in C,* Press et al., Cambridge University Press, 1996). In each case, a measure of the goodness of fit of the unknown to each template is generated, (e.g., a residual value for a least squares approach, or other fit measure dependent on the fitting algorithm used such as one of the "robust" or absolute magnitude methods described by Press et al., supra). If this goodness of fit falls within the pre-determined range for only one of the codes then this is the identity of the unknown code, otherwise the unknown is classified as "no match," or as matching too many templates.

It might be desirable to make the matching process insensitive to absolute intensity variations. This can be done by including a linear or non-linear intensity normalization factor during the matching process, which is varied to generate the lowest residual value or other match parameter for each comparison. The normalization factor can be allowed to vary without limits or can be constrained to be within a given range to limit the amount of correction for intensity variations.

The spectral data can also be normalized spectrally, i.e., shifting the data spectrally in a linear or nonlinear manner, to correct for variations in the wavelength that may occur due to the instrument or due to temperature changes, degradation, or other effects that cause the semiconductor nanocrystals to emit at different wavelengths. Again, the spectral shift factor may be constrained to be within a given range.

When the emission spectrum also contains signal from a reporter or reference semiconductor nanocrystal, e.g., in the case of encoded bead assays, this may be quantitated at the same time, and may also be normalized according to the factors described above. Any spectral overlap from the code into the assay signal may also be corrected for in this way.

Spectral data will often be collected from more windows and/or allowed discrete wavelengths than there are colors of semiconductor nanocrystals present. This allows semiconductor nanocrystals of only slightly differing wavelengths to be used to create the codes. Additional spectral data also makes the classification process more robust than simple one-color, one-data point approaches. An advantage of the pattern matching approach for analysis is that, independent of the method of code creation, any sufficiently different spectra can be used as unique codes. Since unique fingerprints can be obtained for each code based on individual raw spectra, concrete statistical estimates can be used in determinations such as goodness of fit, confidence intervals, and determination of uniqueness. In addition, this method allows for empirical determination of codes following chemical processing as blanks, removing much of the ambiguity associated with pre-formatted idealized code sets.

While the exemplary embodiments have been described in some detail, by way of example and for clarity of understanding, a variety changes, adaptations, and modifications will be obvious to those of skill in the art. Hence, the scope of the present invention is limited solely by the appended claims.

What is claimed is:

1. An identification system comprising:
    a plurality of identifiable elements;
    a plurality of labels, each label associated with a unique or non-unique identifiable element, the labels including reference markers and other markers, the labels generating wavelength/intensity spectra in response to excitation energy; and
    an analyzer for identifying the elements from the wavelength/intensity spectra of the associated labels, the analyzer calibrating at least one of a wavelength of the wavelength/intensity spectra and an intensity of the wavelength/intensity spectra using reference signals generated by the reference markers.

2. The identification system of claim 1, wherein the labels comprise semiconductor nanocrystals.

3. The identification system of claim 2, wherein each reference marker comprises at least one reference semiconductor nanocrystal.

4. The identification system of claim 3, wherein the reference markers comprise a plurality of reference semiconductor nanocrystals, the reference markers of each label generating a reference signal at a reference wavelength with a reference intensity.

5. The identification system of claim 4, wherein the other markers comprise other semiconductor nanocrystals generating other signals at other wavelengths and with other intensities, the reference semiconductor nanocrystals and the other semiconductor nanocrystals of each label being mixed together so that each label is spatially integrated.

6. The identification system of claim 1, wherein the other markers comprise code signal markers which generate code signals different than the reference signals, the wavelength/intensity spectra comprising the marker signals and the code signals, and wherein, for at least one label, the analyzer discretely quantifies the code signals emitted by the code signal markers of the label by comparison of the code signals with the reference signal and by selecting signal characteristics of the code signals from among a plurality of discrete, predetermined signal characteristics.

7. The identification system of claim 6, wherein the reference signal of each label has a reference intensity, and wherein the code signals of the label have code signal intensities, the analyzer discretely quantifying the code signal intensities by comparison to the reference intensity of the label.

8. The identification system of claim 7, wherein the code signal intensities define discrete ratios with the associated reference intensities.

9. The identification system of claim 7, wherein, for each label, the reference intensity signal comprises at least one member selected from a group consisting of: a highest intensity of the wavelength/intensity spectra, a lowest intensity of the wavelength/intensity spectra, a shortest wavelength peak of the wavelength/intensity spectra, and a longest wavelength peak of the wavelength/intensity spectra.

10. The identification system of claim 1, wherein at least some of the reference signals of the labels have common reference wavelengths.

11. The identification system of claim 1, where the reference signals of at least some of the labels have different reference wavelengths.

12. The identification system of claim 11, wherein each reference signal has a reference wavelength, the reference wavelength being a shortest or a longest wavelength of the wavelength/intensity spectra of the label.

13. The identification system of claim 1, wherein the reference signals have reference wavelengths, and wherein the other signals have other wavelengths, the other wavelengths of each label being discretely quantifiable by reference to the reference wavelength of the label.

14. The identification system of claim 1, wherein a wavelength/intensity the spectrum of a first label comprises signals having a plurality of wavelengths, wherein a wavelength/intensity spectrum of a second label comprises signals having the plurality of wavelengths, and wherein the analyzer calibrates wavelength/intensity spectra intensities of the first and second labels based on the reference signals to distinguish the first and second labels.

15. The identification system of claim 1, further comprising at least 1000 labels with associated identifiable elements.

16. The identification system of claim 1, further comprising fewer than 1000 labels with associated identifiable elements.

17. The identification system of claim 1, wherein the analyzer comprises a tangible media embodying a machine readable code, the code comprising a listing of a plurality of distinguishable labels.

18. The identification system of claim 17, wherein the code further comprises a listing of identifiable elements and a correlation between each distinguishable label and an associated identifiable element having the distinguishable label.

19. The identification system of claim 1, wherein the identifiable elements comprise at least one member selected from the group consisting of a composition of matter, a fluid, an article of manufacture, a consumer product, and a component for an assembly.

20. The identification system of claim 1, wherein the markers of each label are spatially intermingled.

21. The identification system of claim 20, wherein the spatially intermingled markers of each label comprise reference quantum dots and at least one associated other quantum dot mixed together within the label.

22. The identification system of claim 1, wherein each label is spatially integrated so that information of the label is independent of a surface area of the label.

23. A method for sensing a plurality of identifiable elements, the method comprising:
labeling each identifiable element with a reference marker and at least one associated other marker;
energizing the markers of a first label from a first identifiable element so that the markers generate signals;
measuring a wavelength/intensity spectrum of the signals; and
identifying a first identifiable element from the spectrum by calibrating a wavelength of the spectrum with reference to a reference wavelength of a reference signal from the reference marker of the first label.

24. The method of claim 23, wherein the labeling step is performed so that the reference marker and the at least one associated other marker of each label are spatially intermingled.

25. The method of claim 24, wherein the labeling step comprises, for each label, mixing reference quantum dots and associate other quantum dots within the label.

26. The method of claim 23, wherein the measured wavelength/intensity spectrum is spatially integrated across the label so that information of the label is independent of a surface area of the label.

27. A library of elements, the library comprising:
a plurality of identifiable elements, each identifiable element having an associated label with a reference marker, the labels generating wavelength/intensity spectra in response to an excitation energy, each wavelength/intensity spectrum including a spectral calibration reference signal from the reference marker.

28. The library of claim 27, wherein the labels comprise semiconductor nanocrystals.

29. The library of claim 27, wherein the semiconductor nanocrystals generate the signals in response to the excitation energy, each reference marker comprising at least one reference semiconductor nanocrystal.

30. The library of claim 29, wherein at least some of the labels comprise at least one other semiconductor nanocrystal generating another signal at another wavelength in response to the excitation energy, the other wavelength different than a reference wavelength of the reference signal, the reference semiconductor nanocrystals being mixed with the other semiconductor nanocrystals in the at least some labels.

31. The library of claim 28, wherein at least some of the labels comprise other markers associated with the reference marker, the other markers generating other signals in response to the excitation energy, the other signals differing from the associated reference signals, and discretely quantifiable by comparison of the other signals with the associated reference signals.

32. The library of claim 31, wherein the reference signals have reference intensities, and wherein the other signals have other intensities, the other intensities each being discretely quantifiable by comparison to the associated reference intensity.

33. The library of claim 32, wherein ratios defined by the other intensities to the associated reference intensities define discrete intensity ratio increments.

34. The library of claim 31, wherein, for each spectrum, the reference intensity is a highest intensity of the spectrum or a lowest intensity of the spectrum.

35. The library of claim 31, wherein at least some of the labels have a first other intensity higher than the reference intensity, and a second other intensity lower than the reference intensity.

36. The library of claim 31, wherein, for each label, the reference signal has a reference wavelength, the reference wavelength being a shortest or a longest wavelength of the spectra of the label.

37. The library of claim 31, wherein the reference signals have reference wavelengths and the other signals have other wavelengths, at least some of the labels including a first other wavelength shorter than the reference wavelength of the label, and a second other wavelength longer than the reference wavelength of the label.

38. The library of claim 31, where the reference signals of at least some of the labels have differing reference wavelengths.

39. The library of claim 31, wherein at least some of the reference signals of the labels have common reference wavelengths.

40. The library of claim 31, wherein the reference signals of the labels have differing reference wavelengths.

41. The library of claim 27, wherein the spectrum of a first label comprises signals having a plurality of wavelengths, wherein a spectrum of a second label comprises signals having the plurality of wavelengths, the first and second spectra having differing overall intensities, the first and second labels distinguishable by calibration of the first and second spectra based on intensities of the reference signals of the first and second signals, respectively.

42. The library of claim 27, further comprising at least 1000 differentiable labels.

43. The library of claim 27, further comprising fewer than 1000 differentiable labels.

44. The library of claim 27, further comprising a tangible media embodying a machine readable code, the code comprising a listing of the labels.

45. The library of claim 44, wherein the code further comprises a listing of identifiable elements and a correlation between each label and an associated identifiable element having the label.

46. The library of claim 27, wherein the identifiable elements comprise at least one member selected from the group consisting of a composition of matter, a fluid, an article of manufacture, a consumer product, a bead, and a component for an assembly.

47. A method comprising:
labeling an identifiable element with a label;
measuring a wavelength/intensity spectrum generated by the label, the wavelength/intensity spectrum comprising a plurality of signals at separated wavelengths; and
identifying the element by selecting a first wavelength range encompassing a first signal of the spectra, and by selecting from among a plurality of discrete predetermined wavelength so as to determine determining a wavelength of the first signal within the first range, the discrete wavelengths within the first range being sufficiently close that two signals at adjacent discrete wavelengths within the first range would substantially overlap.

48. The method of claim 47, wherein the element is labeled by applying at least one semiconductor nanocrystals to the element, the semiconductor nanocrystals generating at least some of the signals in response to excitation energy.

49. The method of claim 47, further comprising selecting a second wavelength range encompassing a second signal of the wavelength/intensity spectra, and by determining a wavelength of the second signal within the second range.

50. The method of claim 49, further comprising, for each other signal of the wavelength/intensity spectra, selecting another wavelength range encompassing the other signal and determining a wavelength of the other signal, wherein no more than one signal of the wavelength/intensity spectra is disposed within each wavelength range.

51. The method of claim 49, wherein the wavelengths of the first and second signals are determined by selecting the wavelengths of the signals from a plurality of discrete wavelengths within the ranges.

52. The method of claim 51, wherein the discrete wavelengths within each range are sufficiently close that two signals at adjacent discrete wavelengths within the range would substantially overlap.

53. The method of claim 51, wherein the discrete wavelengths within the ranges are predetermined.

54. The method of claim 51, wherein the discrete wavelengths within the ranges are separated by about 5 nm or more.

55. The method of claim 51, wherein the discrete wavelengths within the ranges are separated by about 30 nm or more.

56. The method of claim 51, wherein the ranges are separated.

57. The method of claim 56, wherein the ranges are sufficiently separated so that a pair of signals at adjacent discrete wavelengths within adjacent wavelength ranges are sufficiently separated for independent identification of the discrete wavelengths of each signal of the pair.

58. The method of claim 56, wherein the ranges are separated by more than about 30 nm.

59. The method of claim 56, wherein each wavelength range includes at least 5 predetermined discrete wavelengths.

60. The method of claim 59, wherein there are at least three non-overlapping wavelength ranges.

61. The method of claim 47, further comprising identifying a plurality of elements in response to wavelength/intensity spectra generated from other labels associated with the elements by selecting wavelength ranges encompassing signals of the wavelength/intensity spectra, and by determining wavelengths of the signals within the ranges.

62. The method of claim 61, wherein no more than one signal from each wavelength/intensity spectrum is disposed within each wavelength range.

63. The method of claim 61, further comprising establishing predetermined wavelength ranges, the plurality of elements being identified using the predetermined wavelength ranges.

64. The method of claim 63, further comprising establishing predetermined discrete wavelengths within the predetermined wavelength ranges, the wavelengths of the signals being selected from the predetermined wavelengths.

65. The method of claim 61, further comprising rejecting labels having excessive overlap between adjacent discrete wavelengths from different adjacent wavelength ranges.

66. The method of claim 51, wherein the wavelength determining step comprises a binary determination between a presence of the discrete wavelength and an absence of the discrete wavelength.

67. The method of claim 66, wherein the wavelength/intensity spectra of the labels comprise a plurality of separated luminescent signals including signals within the first range, the first range being predetermined, and a second predetermined wavelength range, a discrete wavelength of at least one of the signals of each wavelength/intensity spectrum being different than a discrete wavelength of the wavelength/intensity spectrum of every other wavelength/intensity spectrum.

68. The method of claim 61, further comprising measuring a discrete intensity of the discrete wavelength.

69. The method of claim 61, wherein the label and the other labels comprise intermingled markers.

70. The method of claim 69, wherein the signals of a first label are encompassed within the first predetermined wavelength range, and wherein the signals of a second label are encompassed within another wavelength range such that the wavelength/intensity spectra of the first and second labels are separated.

71. A method for sensing a plurality of intermingled labels, the method comprising:

energizing the labels so that the labels generate signals;

identifying a first label by measuring a first discrete wavelength from among a plurality of predetermined discrete wavelengths within a first wavelength range; and identifying a second label by measuring a second discrete wavelength from among a plurality of predetermined discrete wavelengths within a second wavelength range, the first and second ranges being separated, the discrete wavelengths within each range being sufficiently close that two signals at adjacent discrete wavelengths within the range would substantially overlap.

72. The method of claim 71, further comprising adding a plurality of labels to a fluid at an associated plurality of process steps so that the labels indicate the process steps performed to the fluid.

73. An inventory system comprising:

a plurality of identifiable elements; and a plurality of labels having markers, each label associated with an element, each marker generating a signal when energized so that each label emits an identifiable wavelength/intensity spectrum, at least some of the wavelength/intensity spectra comprising a plurality of the signals, each signal of the wavelength/intensity spectra having a discrete wavelength selected from within a dedicated wavelength range, the discrete wavelengths within the range being sufficiently close that two signals at adjacent discrete wavelengths within the range would substantially overlap, the ranges sufficiently separated so that the signals in different ranges are independently identifiable.

74. The inventory system of claim 73, further comprising an analyzer having a signal sensor in optical communication with the signals and a processor, the processor selecting a first discrete wavelength from among a plurality of discrete wavelengths within a first wavelength range in response to a first signal of a first wavelength/intensity spectra, the processor selecting a second discrete wavelength from among a plurality of adjacent discrete wavelengths within a second wavelength range, the first and second ranges being separated, the processor having a database of the identifiable elements and the associated labels and generating an element identification signal in response to the first and second selected wavelengths.

75. The inventory system of claim 74, wherein the labels comprises at least one bead including a matrix, the markers including at least one semiconductor nanocrystal supported in the matrix.

76. The inventory system of claim 73, wherein each label comprises at least one bead, and wherein at least some of the beads have a plurality of markers comprising an associated plurality of semiconductor nanocrystal populations, each population including a plurality of semiconductor nanocrystals that emit a substantially uniform wavelength when energized so as to define the signal of the marker.

77. The inventory system of claim 73, wherein each label has a unique wavelength/intensity spectra including no more than one discrete wavelength selected from a plurality of predetermined wavelengths within each of a plurality of separated wavelength ranges.

78. A method comprising:

labeling an identifiable element with a label;

measuring a wavelength/intensity spectrum generated by the label, the wavelength/intensity spectrum comprising a plurality of signals; and identifying the element by;

selecting a first wavelength range encompassing a first signal of the spectra;

determining a first wavelength of the first signal within the first range by selecting the first wavelength from a first plurality of discrete predetermined wavelengths within the first range;

selecting a second wavelength range encompassing a second signal of the spectra, the second wavelength range being separated from the first wavelength;

determining a second wavelength of the second signal within the second range by selecting the second wavelength from a second plurality of discrete predetermined wavelengths within the second range;

the discrete wavelengths within each range being sufficiently close that two signals at adjacent discrete wavelengths within the range would substantially overlap.

* * * * *